United States Patent
Konno

(10) Patent No.: US 10,292,668 B2
(45) Date of Patent: May 21, 2019

(54) X-RAY SCANNING APPARATUS

(71) Applicant: HITACHI, LTD., Tokyo (JP)

(72) Inventor: Yasutaka Konno, Tokyo (JP)

(73) Assignee: HITACHI, LTD., Tokyo (JP)

( * ) Notice: Subject to any disclaimer, the term of this patent is extended or adjusted under 35 U.S.C. 154(b) by 510 days.

(21) Appl. No.: 15/122,981

(22) PCT Filed: Mar. 17, 2015

(86) PCT No.: PCT/JP2015/057802
§ 371 (c)(1),
(2) Date: Sep. 1, 2016

(87) PCT Pub. No.: WO2015/146691
PCT Pub. Date: Oct. 1, 2015

(65) Prior Publication Data
US 2017/0105688 A1    Apr. 20, 2017

(30) Foreign Application Priority Data

Mar. 26, 2014   (JP) .................................. 2014-064549

(51) Int. Cl.
*A61B 6/00* (2006.01)
*A61B 6/03* (2006.01)
*G01T 1/29* (2006.01)

(52) U.S. Cl.
CPC ............ *A61B 6/4241* (2013.01); *A61B 6/032* (2013.01); *A61B 6/482* (2013.01); *A61B 6/5205* (2013.01); *A61B 6/585* (2013.01); *G01T 1/2985* (2013.01)

(58) Field of Classification Search
CPC ..... A61B 6/4241; A61B 6/482; A61B 6/5205; A61B 6/585; G01T 1/17; G01T 1/247
See application file for complete search history.

(56) References Cited

U.S. PATENT DOCUMENTS

| | | | |
|---|---|---|---|
| 2013/0287175 A1 | 10/2013 | Nagai | |
| 2014/0211910 A1* | 7/2014 | Subramanian | .......... G01T 7/005 378/5 |
| 2014/0326894 A1* | 11/2014 | Abraham | ................. H04N 5/32 250/394 |

FOREIGN PATENT DOCUMENTS

| | | |
|---|---|---|
| JP | 2011-85479 | 4/2011 |
| JP | 2013-19698 | 1/2013 |
| WO | WO 2013/048436 A1 | 4/2013 |

OTHER PUBLICATIONS

International Search Report in connection with PCT/JP2015/057802.

* cited by examiner

*Primary Examiner* — Dani Fox
(74) *Attorney, Agent, or Firm* — Cooper & Dunham LLP

(57) ABSTRACT

In an X-ray scanning apparatus mounted with a photon counting type radiation detector, a data processing device of the X-ray scanning apparatus includes a correction unit that corrects a digital output value in each of the plurality of energy ranges with respect to each X-ray detection element in order to obtain an accurate projection image by correcting a counting error of the number of X-ray photons in each energy range. The correction unit includes an inflow amount calculation portion that calculates a digital amount corresponding to X-ray photons which flow from a certain X-ray detection element to another X-ray detection element, and an energy shift inflow amount/outflow amount calculation portion that calculates a digital amount corresponding to X-ray photons which flow into a high energy range due to energy shift in a single X-ray detection element, and performs correction by using the digital amounts calculated by the calculation portions.

14 Claims, 13 Drawing Sheets

FIG. 3
(a) 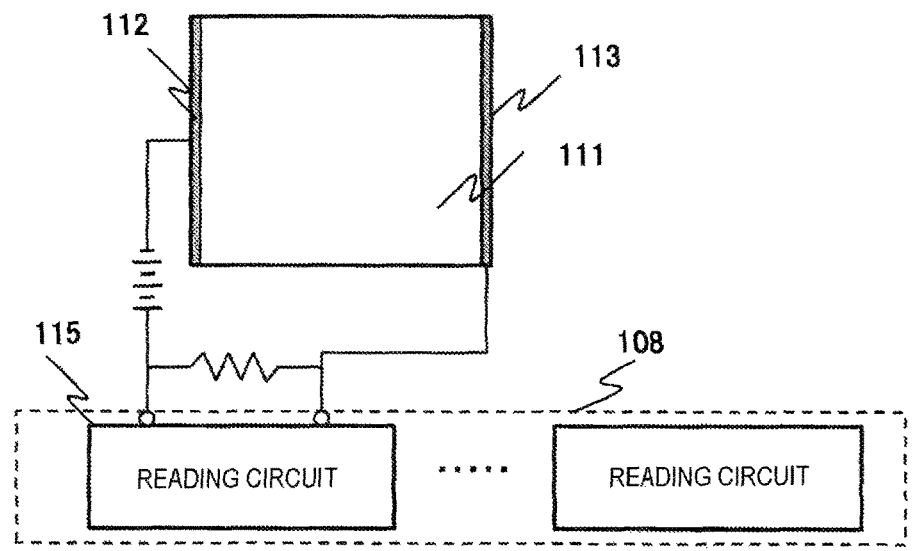
(b) 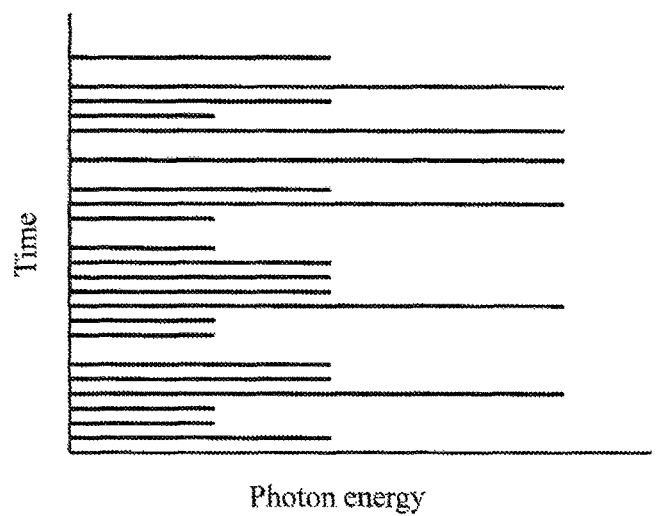
(c) 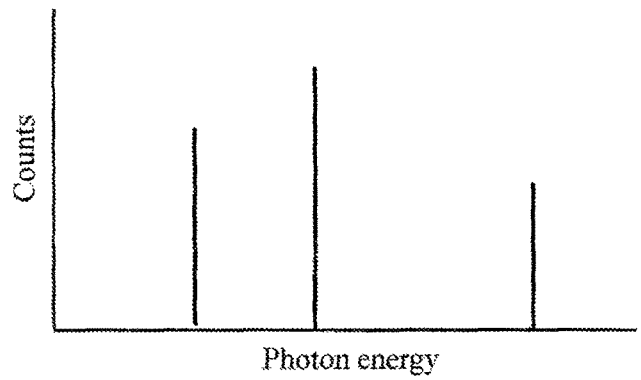

X-RAY SCANNING APPARATUS

TECHNICAL FIELD

The present invention relates to an image scanning apparatus such as an X-ray CT apparatus, and particularly to an X-ray scanning apparatus mounted with a photon counting type X-ray detector.

BACKGROUND ART

An X-ray CT apparatus is an apparatus which calculates an X-ray absorption coefficient on the basis of an X-ray transmission image (hereinafter, referred to as a projection image) of an object obtained through scanning from a plurality of directions, and thus obtains a tomographic image (hereinafter, referred to as a reconstructed image) of the object. The apparatus is widely used in a medical field or a non-destructive inspection field.

A so-called integral X-ray detector is mounted in many current medical X-ray CT apparatuses. In the integral X-ray detector, X-rays are converted into light by a scintillator, the light is converted into an electric charge by a photodiode, the electric charge is converted into a digital signal by a reading circuit, and the digital signal is output. The reading circuit integrates the electric charge for each view so as to obtain a digital signal. A lot of X-ray photons are incident during one view, and an obtained signal quantity is a signal quantity corresponding to a sum total of energy of incident X-rays. Thus, energy information of each of the incident X-ray photons cannot be known.

On the other hand, as in NPL 1, in recent years, an X-ray CT apparatus mounted with a photon counting type X-ray detector has been developed. The X-ray detector includes an X-ray detection element having a detection layer of a semiconductor such as CdTe, and a reading circuit which classifies and obtains a digital signal for each energy range according to energy of incident X-ray photons. In this X-ray detector, if X-rays are incident on the X-ray detection element, first, an electric charge corresponding to energy of X-ray photons is generated in the detection layer. Next, the reading circuit reads the electric charge at a high speed at which each of the X-ray photons can be read, and classifies and counts the number of X-ray photons for each of several energy ranges according to energy of the incident X-ray photons. In this case, incident energy is identified by using an amount of generated electric charge. The detection is similarly performed on each of a plurality of X-ray photons, the number of X-ray photons is counted in each energy range, and the counted number is converted into a digital signal. Through the measurement, a projection image can be obtained for each energy range, and thus a reconstructed image can be obtained for each energy range by using the projection image.

CITATION LIST

Non-Patent Literature

NPL 1: David P. Cormode, Ewald Roessl, Axel Thran, et al. Analysis with Multicolor CT and Target Gold Nanopartides. Radiology 2010; 256(3): 774 to 782

SUMMARY OF INVENTION

Technical Problem

In the photon counting type X-ray detector, when X-rays are detected in the detection layer, a lot of electric charge is generated, but, in this process, the X-rays perform interaction with the detection layer multiple times, and move to some extent until the X-rays are completely detected. Thus, electric charge generated by a single X-ray photon may be detected by a plurality of pixels (detection elements). In this case, the detected electric charge of the X-rays is distributed to the respective pixels, and thus it is wrongly determined that two X-ray photons having energy lower than that of the incident X-ray photon are detected. Therefore, there may be a case where the X-ray photon is measured as an X-ray photon in a different energy range, or a case where X-ray photons which are not incident are erroneously counted.

In addition, there is a case where a fluorescent X-ray generated when an X-ray is detected in the detection layer may be detected by other pixels. Also in this case, counting loss of incident X-rays, detection in a different energy range, counting of X-ray photons which are hot directly incident, and the like occur.

Such a counting error can be corrected through simultaneous measurement. This method is performed in, for example, a positron emission tomography (PET) apparatus, and, in a case where X-ray photons are incident on a target element, and a signal is also detected in an adjacent element at the same time, the signal detected in the adjacent element is regarded as some of the X-ray photons incident on the target element. However, in this method, when an incidence rate (a dose of X-rays which are incident per unit time) is high, there is a high probability that other X-ray photons may be simultaneously incident on the adjacent element, and thus errors are likely to occur. In addition, time required in a process for determining the simultaneousness is taken, and thus it is hard to apply the method to an apparatus in which X-rays are incident on an X-ray detector at a high X-ray incidence rate, such as the X-ray CT apparatus.

Some X-rays which have been incident on the detection layer are transmitted through the detection layer during interaction with the detection layer. In this case, it is wrongly determined that a single X-ray photon having energy lower than that of an original X-ray is incident. Thus, there may be a case where an X-ray photon is counted as an X-ray photon in a different energy range.

As mentioned above, if a counting error in the number of X-ray photons in each energy range occurs, an accurate projection Image cannot be obtained in each energy range. A signal flows into a target element from an adjacent element, and thus there is a probability that an image may be blurred or the resolution thereof may be reduced. Quantitativeness of a CT value may be reduced or an artifact may occur in a reconstructed image which is created on the basis of such a projection image.

Solution to Problem

In order to solve the above-described problems, an X-ray scanning apparatus of the invention includes correction means by taking into consideration a movement proportion of X-ray photons inflowing and outflowing between X-ray detection elements, and a proportion of X-ray photons counted as X-ray photons measured in a low energy region due to energy shift in an X-ray detection element.

In other words, according to the invention, there is provided an X-ray scanning apparatus including an X-ray detector that is formed of a plurality of photon counting type X-ray detection elements each of which detects an X-ray photon and classifies an energy level of the X-ray photon into a plurality of energy ranges to perform measurement; a signal collecting unit that collects outputs from the X-ray detection elements so as to obtain digital output values; and a data processing device that corrects digital output values of the X-ray detection elements, and creates projection data by using the corrected digital output values, in which the data processing device includes a correction unit that corrects a digital output value in each of the plurality of energy ranges with respect to each of the X-ray detection elements. The correction unit includes a counting correction portion that corrects the digital output value by using a parameter indicating a movement proportion, obtained in advance, between X-ray detection elements, and a parameter indicating an energy shift proportion in an X-ray detection element.

In an aspect of the invention, the correction unit includes an inflow amount calculation portion that calculates a digital amount corresponding to an amount of a signal which is caused by an X-ray photon incident on another X-ray detection element, with energy higher than a detection target energy range of a single correction target X-ray detection element and which flows into the correction target X-ray detection element, and the Correction unit removes the digital amount calculated by the inflow amount calculation portion from the digital output value (first aspect).

In another aspect of the invention, the correction unit includes an energy shift inflow amount calculation portion that calculates a digital amount corresponding to an X-ray photon which energy-shifts from an energy range higher than a detection target energy range to the detection target energy range in a single X-ray detection element, and removes the digital amount calculated by the energy shift inflow amount calculation portion from the digital output value (second aspect).

In still another aspect of the invention, the correction unit includes an energy shift outflow amount calculation portion that calculates a digital amount corresponding to an X-ray photon which is incident on a single X-ray detection element and energy-shifts to an energy range lower than the detection target energy range, and adds the digital amount calculated by the energy shift outflow amount calculation portion to the digital output value (third aspect).

The invention includes any combination of the above first to third aspects.

Advantageous Effects of Invention

According to the invention, it is possible to prevent the number of incident X-ray photons in each energy range from being wrongly measured and thus to obtain an accurate projection image. It is possible to prevent a reduction in quantitativeness of a CT value or the occurrence of an artifact in a reconstructed image which is created on the basis of the projection image.

BRIEF DESCRIPTION OF DRAWINGS

FIGS. 3(a) to 3(c) are diagrams illustrating a section and an operation of the X-ray detection element.

DESCRIPTION OF EMBODIMENTS

Hereinafter, embodiments of the invention will be described in detail with reference to the drawings. In the following description, the invention will be described by exemplifying an X-ray CT apparatus, but the invention is applicable to X-ray scanning apparatuses other than the X-ray CT apparatus.

Figure 1:
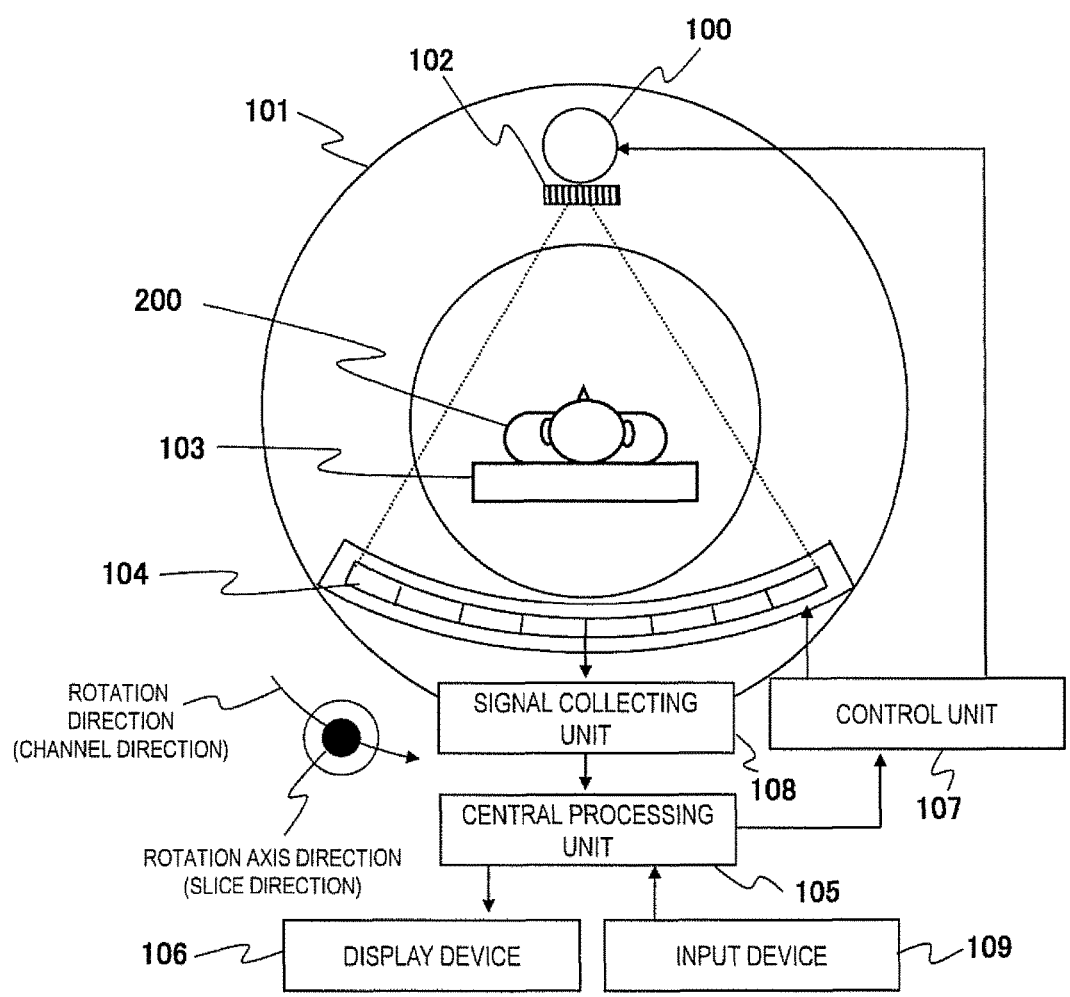
FIG. 1 is a schematic diagram illustrating an X-ray CT apparatus according to an embodiment of the invention.

FIG. 1 is a diagram illustrating the entire summary of an X-ray CT apparatus to which the invention is applied. The X-ray CT apparatus illustrated in FIG. 1 is configured to include an X-ray source 100, an X-ray collimator 102, X-ray detectors 104, a signal collecting unit 108, a central processing unit 105, a display device 105, an input device 109, a control unit 107, a gantry rotation unit 101, and a bed top plate 103.

A plurality of X-ray detectors 104 are disposed in an arc shape substantially centering on the X-ray source 100, and are mounted in the gantry rotation unit 101 along with the X-ray source 100. For simplification of description, FIG. 1 illustrates a case where the number of X-ray detectors 104 is eight, but the number of the X-ray detectors 104 is any number, and is forty, for example, in an actual apparatus. X-ray grids (not illustrated in FIG. 1) are provided in front of the X-ray detectors 104, and prevent X-rays scattered by an object 200 or the like among X-rays applied from the X-ray source 100, from being incident on the X-ray detectors 104.

Figure 2:
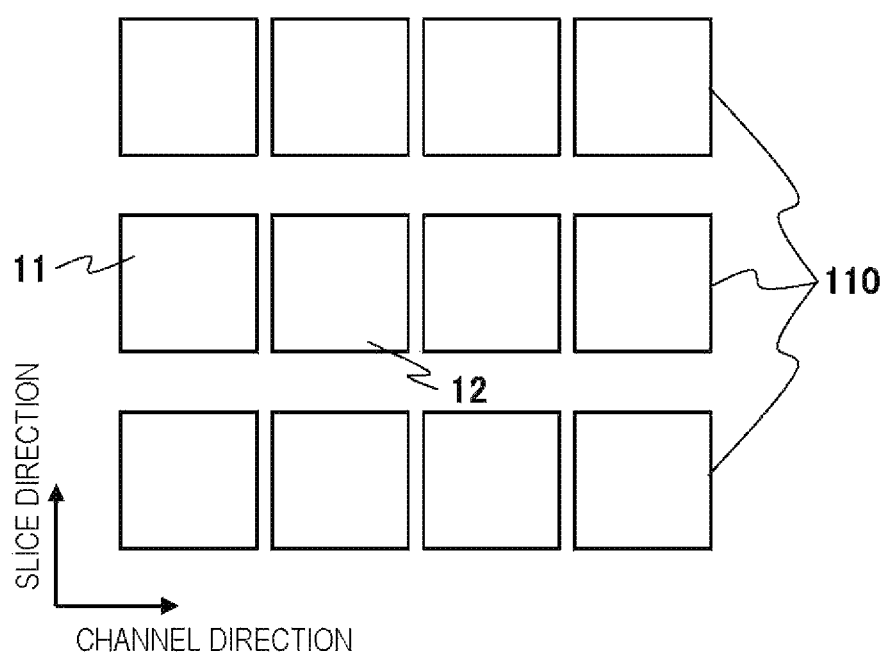
FIG. 2 is a diagram for explaining an example of arrangement of X-ray detection elements 110.

Each of the X-ray detectors 104 has a structure in which photon counting type X-ray detection elements are disposed in a two-dimensional manner in a channel direction and a slice direction, for example, as illustrated in FIG. 2. FIG. 2 illustrates some X-ray detection elements 110 disposed in the X-ray detector 104, and illustrates that four X-ray detection elements in the channel direction and three X-ray detection elements in the slice direction are cut out. The X-ray detection elements 110 are disposed so that the channel direction matches a rotation direction of the X-ray detectors 104, and the slice direction matches a rotation axis direction thereof.

Each of the X-ray detection elements 110 has a structure in which positive and negative electrodes 112 and 113 are disposed with a detection layer 111 interposed therebetween, and a reading circuit 115 (signal collecting unit 108) is connected to the electrodes, as illustrated in FIG. 3(a). The detection layer 111 is made of a semiconductor material such as cadmium telluride (CdTe), cadmium zinc telluride (CdZnTe), or silicon (Si), and detects an incident X-ray photon so as to generate electric charge with an amount corresponding to energy of the X-ray photon. The reading circuit 115 reads the electric charge generated by the detection layer 111, and compares an energy level of an electric signal caused by the electric charge with a preset energy level so as to determine an energy range of the energy of the incident X-ray photon.

The reading circuit 115 performs this determination on each incident X-ray photon, and classifies a plurality of energy ranges from each other during one view, and counts the number of X-ray photons in each energy range. An electric signal which is output from the reading circuit 115 of each X-ray detection element 110 and corresponds to each counted number is output as a digital signal by the signal collecting unit 108. FIGS. 3(b) and 3(c) illustrate a state in which an energy range is divided into three ranges, and the number of X-ray photons is counted, and signals corresponding thereto, as examples. With this structure of the X-ray detectors 104, X-rays are detected in the detection layer 111, and then a digital signal (digital output value) corresponding to the number of X-ray photons can be obtained in each energy range. The number of energy ranges is not particularly limited as long as the number thereof is two or larger, but, hereinafter, for simplification of description, a description will be made of a case where an energy range is divided into two ranges such as a low energy range and a high energy range.

Figure 4:
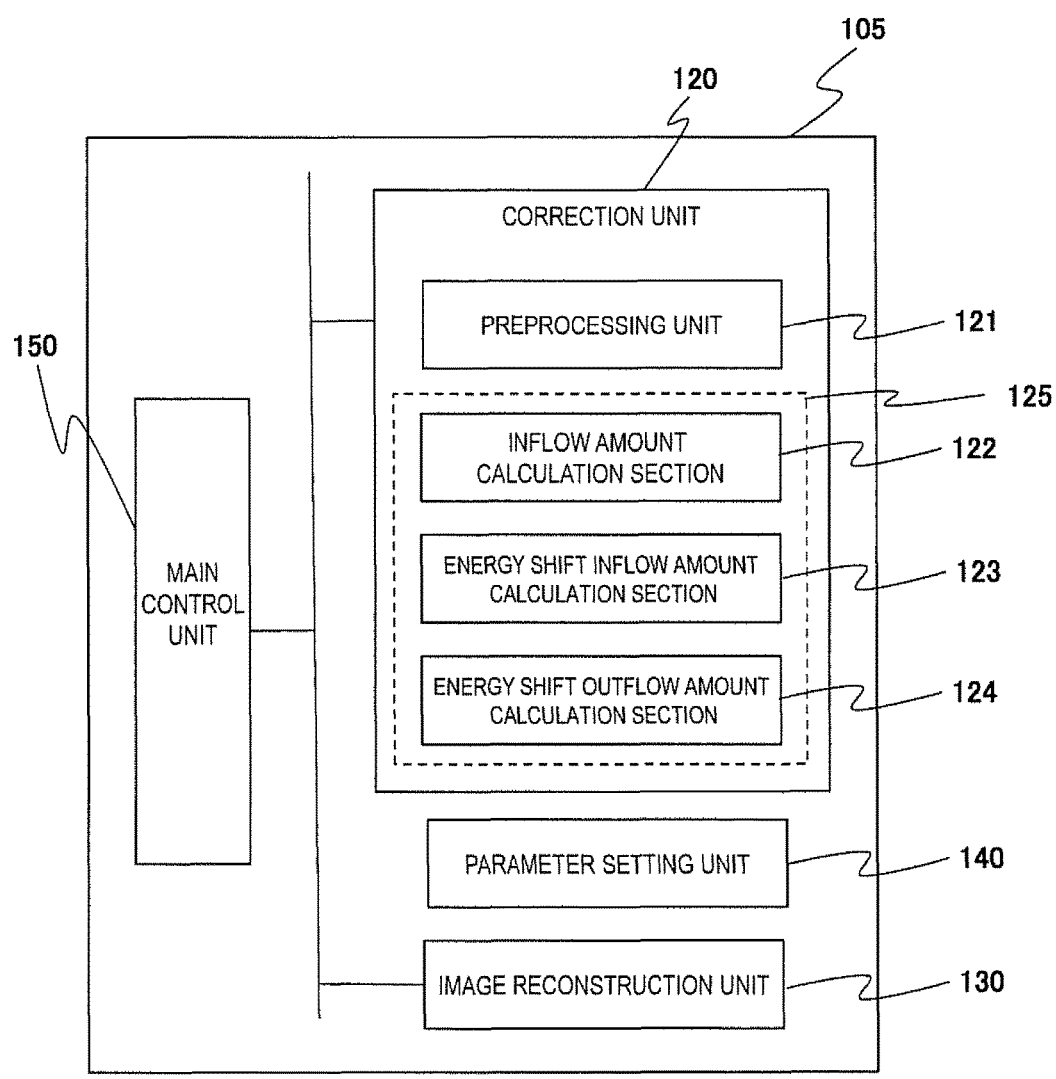
FIG. 4 is a functional block diagram of a data processing device.

The central processing unit 105 mainly processes the digital signal output from the signal collecting unit 108, and performs data processing such as correction or image reconstruction. FIG. 4 is a functional block diagram of the central processing unit 105 which functions as a data processing device. As illustrated in FIG. 4, the central processing unit (data processing device) 105 includes a correction unit 120, an image reconstruction unit 130, a parameter setting unit 140, and a main control unit 150 which controls a flow of data in each unit, and performs various calculations required in image creation. The central processing unit performs each calculation by executing a corresponding calculation program. The calculation program is stored in the central processing unit 105 in advance. Alternatively, the calculation program is uploaded to the central processing unit by using a portable medium or through communication, and is executed. Although not illustrated in FIG. 4, a storage device 160 storing data or parameters 141 required in various calculations is provided in the central processing unit 105 as an internally and/or externally attached device.

The correction unit 120 includes a preprocessing unit 121, and a counting correction portion 125 which corrects the number of X-ray photons counted in each element of the X-ray detector 104. The preprocessing unit 121 performs a process for removing an error which depends on the apparatus or removing signals which are not related to the object, and performs a well-known preprocess such as LOG conversion or air correction on data from the signal collecting unit 108. The counting correction portion 125 calculates a digital amount to be removed from an output value or a digital amount to be supplemented in each energy range for each detection element forming the X-ray detector 104, and includes, in the illustrated example, an inflow amount calculation section 122, an energy shift inflow amount calculation section 123, and an energy shift outflow amount calculation section 124. The counting correction portion 125 corrects a digital output value of the X-ray detectors 104, which is input from the signal collecting unit 108, by using digital amounts calculated by the respective calculation sections 122 to 124. A function of each calculation section will be described later in detail.

The image reconstruction unit 130 performs calculation such as a well-known filtered back projection method and successive approximation method on the basis of projection data corrected in the correction unit 120 in each energy range, so as to reconstruct a CT image. The parameter setting unit 140 sets a parameter defined on the basis of a parameter which is directly input from the input device 109, an input condition, or the like, and sends the parameter to the correction unit 120 or the image reconstruction unit 130.

The display device 106 displays an image or the like created by the image reconstruction unit 130, or displays a GUI to be operated by an operator. The input device 109 may include a keyboard, a mouse, and various operation buttons for giving instructions for starting and finishing scanning.

Next, a description will be made of a scanning method (hereinafter, referred to as actual scanning) of acquiring a reconstructed image by scanning the object 200 and a processing method on the basis of the above-described configuration. First, if starting of actual scanning is input via the input device 109, X-rays are applied from the X-ray source 100. The X-rays undergo restriction of an irradiation field in the X-ray collimator 102 so as to be applied to the object 200 placed on the bed top plate 103, and X-rays transmitted through the object 200 are detected by the X-ray detectors 104.

This scanning is repeatedly performed while changing an irradiation angle of X-rays relative to the object 200 by rotating the gantry rotation unit 101 in the rotation direction, and thus digital signals corresponding to 360 degrees are acquired. The scanning is performed during a plurality of views, for example, every 0.4 degrees. During that time, the control unit 107 controls a position of an X-ray focal position. The digital signals obtained in the above-described way are collected by the signal collecting unit 108. The data collected by the signal collecting unit 108 will be hereinafter referred to as raw data 143.

Figure 5:
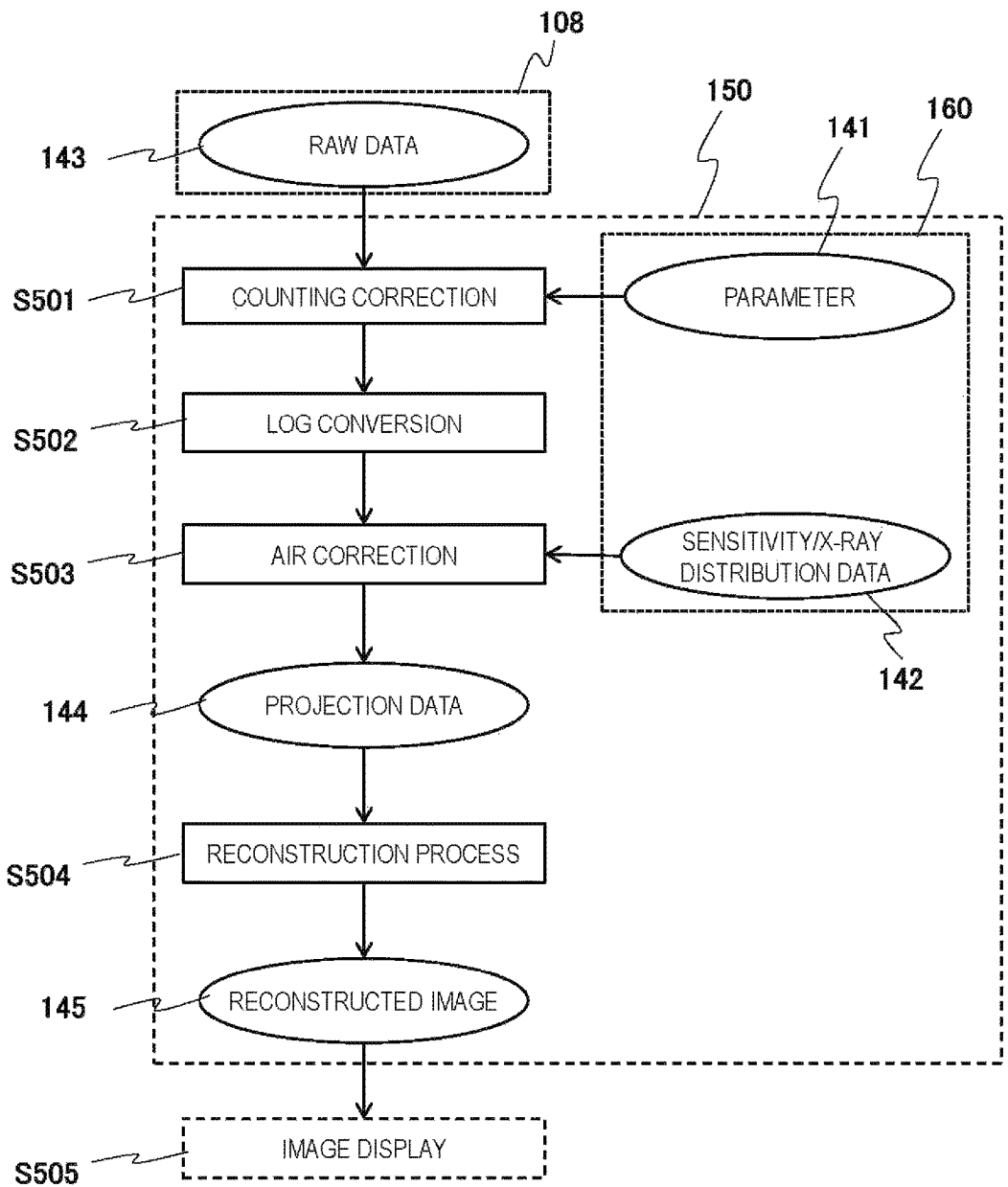
FIG. 5 is diagram illustrating an example of a flow of data processing.

The raw data 143 is sent to the central processing unit 105 so as to undergo a correction process. FIG. 5 illustrates procedures of the correction process in the central processing unit 105. In the correction process, first, counting correction is performed on the raw data 143 received from the signal collecting unit 108 (S501). As will be described in detail, in the counting correction, a counted number of X-ray photons is corrected for each digital signal in the low energy range and the high energy range. In this case, the parameters 141 stored in the storage device 160 are read, and then calculation in the correction process is performed.

Next, LOG conversion is performed (S502). If an unconverted value is indicated by X, and a converted value is indicated by Y, the LOG conversion is expressed by, for example, Equation (1). Here, a and b are coefficients as constants.

$$Y = a\ \mathrm{LOG}(X) + b \tag{1}$$

Next, air correction is performed (S503). This correction is performed, for example, by subtracting sensitivity/X-ray distribution data 142 which is created in advance before the present scanning and is stored in the storage device 160, from raw data having undergone the LOG conversion. For example, X-rays are applied from the X-ray source 100 so that raw data is acquired for each energy level in a state in which the object 200 is not present, and the counting correction, an addition averaging process for a view, and LOG conversion are performed on the raw data, so that the sensitivity/X-ray distribution data 142 is created.

After projection data 144 is obtained through the above-described process, a reconstruction process is performed (S504), and a reconstructed image 145 for an X-ray absorption coefficient distribution of the object 200 is created, for example, in each of the low energy range and the high energy range. Finally, the reconstructed image 145 is displayed on the display device 106 (S505).

The correction process illustrated in FIG. 5 is an example, and does not limit the invention. For example, there may be a case where correction order differs, a case where another correction is added, or a case where the air condition S503 is omitted.

Next, a process in the counting correction S501 will be described in detail. In this process, at least one correction process among an inflow amount removal process, an energy shift inflow amount removal process, and an energy shift outflow amount supplementing process is performed. The correction process is performed on all of the X-ray detection elements forming the X-ray detector, but, in the following description, a correction process on a single X-ray detection element 11 (hereinafter, referred to as a target element 11) illustrated in FIG. 2 will be described.

Figure 6:
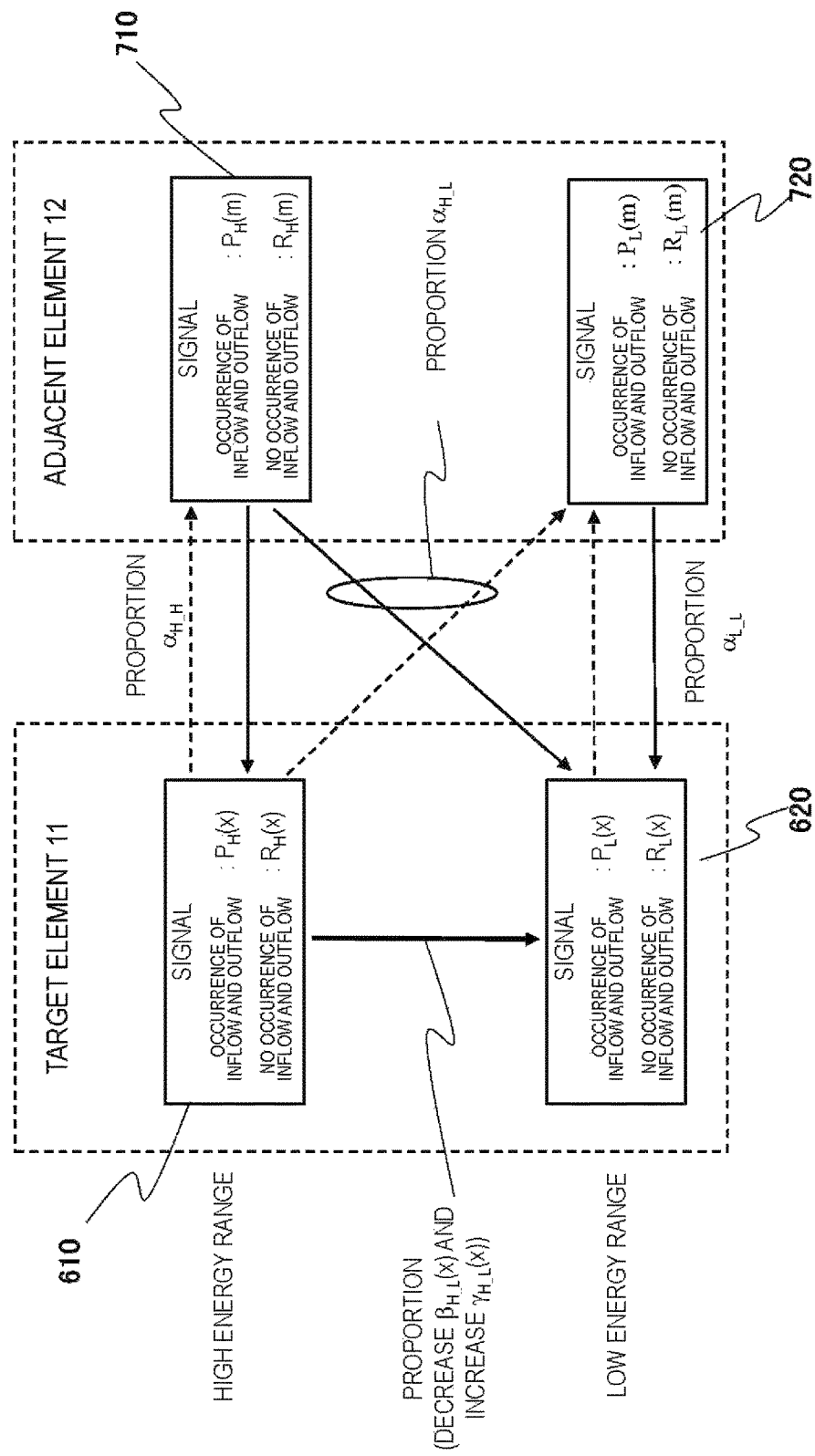
FIG. 6 is a diagram illustrating inflow and outflow of signals between elements and in the elements.

First, the cause that a counted number measured for the target element 11 is inaccurate will be described with reference to FIG. 6. In FIG. 6, a signal in the high energy range of the target element 11 is indicated by a box 610, and a signal in the low energy range is indicated by a box 620. Similarly, a signal in the high energy range of an adjacent element 12 is indicated by a box 710, and a signal in the low energy range is indicated by a box 720.

If the single target element 11 counts the number of X-ray photons in a predetermined energy region, the counted number (digital amount) includes not only a counted number of X-ray photons (detection target photons) in a detection target energy region, incident on the target element 11, but also a counted number of (1) X-ray photons (inflow photons) (in FIG. 6, an arrow indicated by a thin solid line) inflowing from the adjacent element 12 and (2) X-ray photons (energy shift photons) (in FIG. 6, an arrow indicated by a thick solid line) in an energy region higher than the detection target energy region, incident on the detection element and causing energy shift. The counted number of the inflow photons and the energy shift photons is required to be removed from a measured value.

Inherently, there are X-ray photons which are X-ray photons in a predetermined energy region, incident on the target element 11, and are not measured as X-ray photons in the detection target energy region due to energy shift to a lower energy region. A measured value is required to be supplemented with a counted number of the X-ray photons which are not measured.

Here, in the photon counting type detector, unlike crosstalk in an integral detection element, inflow and outflow due to energy shift are unidirectional movement from a high energy range to a low energy range, and thus an X-ray photon in a lower energy range does not flow into the same element or an adjacent element in a higher energy range. An X-ray photon in the same energy range may flow into and out of elements adjacent to each other. In a case where an X-ray photon in a higher energy range flows into an adjacent element, and is thus counted as an X-ray photon, a counted number is an inflow amount required to be removed on the inflow side, but, on the outflow side (target element), the X-ray photon has already been counted, and thus a counted number is not required to be supplemented since only energy shift is taken into consideration.

In the correction process of the present embodiment, counting correction is performed by taking into consideration such behavior (inflow or out flow of a signal) of an X-ray photon in the photon counting type detector. Hereinafter, embodiments of the correction process will be described.

First Embodiment

The present embodiment is characterized in terms of performing all three processes such as removal of an inflow amount from another element, removal of an energy shift inflow amount in the same element, and interpolation of a value which is not measured in the same element. Hereinafter, counting correction according to the present embodiment will be described with reference to a flow illustrated in FIG. 7.

<Determination of Parameters> (S5011)

In the correction process, first, parameters indicating a movement proportion of X-ray photons between elements, and parameters indicating a proportion of energy shift in the same element are obtained. The former parameters include three kinds of parameters such as a parameter $\alpha_{H\_H}$ indicating a proportion of X-ray photons measured in a high energy range of the target element 11 among signals incident on the adjacent element 12 in a high energy range, a parameter $\alpha_{H\_L}$ indicating a proportion of X-ray photons measured in a low energy range of the target element 11 among signals incident on the adjacent element 12 in a high energy range, and a parameter $\alpha_{L\_L}$ indicating a proportion of X-ray photons measured in a low energy range of the target element 11 among signals incident on the adjacent element 12 in a low energy range, which are obtained for each element.

The parameters indicating a proportion of energy shift are a parameter $\beta_{H\_L}(x)$ indicating a proportion of X-ray photons measured in a low energy range among incident X-ray photons having energy in a high energy range and indicating a decrease proportion of the high energy range, and a parameter $\gamma_{H\_L}(x)$ indicating an increase proportion of the low energy range, for a single element. $\beta_{H\_L}(x)$ and $\gamma_{H\_L}(x)$ are generally the same as each other, but may be different from each other. For example, this case is a case where energy is lost in a high energy range but remains therein, or a case where lost energy is measured in a low energy range.

Methods of obtaining the parameters roughly include three methods. A first method is a method using simulation, a second method is a method of performing actual measurement, and a third method is a method in which parameters are actually measured for one or several elements, and are estimated for other elements. These methods may be combined with each other as appropriate.

In the simulation method, for example, Monte Carlo simulation is performed in which the target element 11 and the adjacent element 12 are simulated as in the arrangement in FIG. 2. First, the number of X-ray photons flowing into the target element when X-rays are incident on the adjacent element by taking into consideration energy is counted, and thus the parameters $\alpha_{H\_H}$, $\alpha_{H\_L}$, and $\alpha_{L\_L}$ can be obtained. A counting result of the number of X-ray photons obtained when X-rays are incident on the target element 11 by taking energy into consideration is compared with spectra of the input X-rays, and thus the parameters $\beta_{H\_L}$ and $\gamma_{H\_L}$ can be obtained.

In a case of the actual measurement method, first, spectra of applied X-rays are measured. Consequently, proportions $r_H(x)$ and $r_L(x)$ (where $r_H(x)+r_L(x)=1$) of counts in the high energy range and the low energy range in a case where there is no object are estimated. Here, x indicates a position of a target element.

Next, X-rays are incident on the target element 11, and digital output values $P_H(x)$ and $P_L(x)$ in the high energy range and the low energy range are actually measured. At this time, in order to prevent inflow of a signal from other X-ray detection elements, the X-rays are narrowed and applied in a dot shape or a thin slit shape via a pin hole or a slit as illustrated in FIG. 8(a) or 8(b). Measurement proportions $\beta_{H\_L}(x)$ and $\gamma_{H\_L}(x)$ of X-ray photons in the low energy range are calculated on the basis of this result. In this case, if there is no inflow or outflow of a signal, a count measured in the high energy range is preferably formed of $r_H(x)(P_H(x)+P_L(x))$, but, if there is inflow or outflow, $P_H(x)$ is measured. Therefore, a signal from the high energy range is reduced by $r_H(x)(P_H(x)+P_L(x))-P_H(x)$. Meanwhile, if this amount is indicated by using the proportion $\beta_{H\_L}(x)$, this leads to $\beta_{H\_L}(x)r_H(x)(P_H(x)+P_L(x))$, and thus it can be seen that $\beta_{H\_L}(x)$ may be expressed as in the following Equation (2-1).

On the other hand, a signal into the low energy range increases by $r_L(x)(P_H(x)+P_L(x))-P_L(x)$, and, if this amount is indicated by using $\gamma_{H\_L}(x)$, this leads to $\gamma_{H\_L}(x)r_L(x)(P_H(x)+P_L(x))$, and thus it can be seen that $\gamma_{H\_L}(x)$ may be expressed as in the following Equation (2-2).

$$\beta_{H\_L} = \frac{r_H(x)P_L(x) - r_L(x)P_H(x)}{r_H(x)(P_H(x) + P_L(x))} \quad (2\text{-}1)$$

$$\gamma_{H\_L} = \frac{r_L(x)P_H(x) - r_H(x)P_L(x)}{r_L(x)(P_H(x) + P_L(x))} \quad (2\text{-}2)$$

When there is an object, spectra of X-rays incident on the X-ray detectors 104 change, but, here, an approximate value in a case where there is no object is used.

Next, as illustrated in FIG. 8(c) or 8(d), X-rays with a slit shape or a pin hole shape narrowed at least in the channel direction are applied so that digital output values $P_H(m)$ and $P_L(m)$ of the adjacent element 12 are measured, and thus $\alpha_{H\_H}$, $\alpha_{H\_L}$, and $\alpha_{L\_L}$ are measured. Here, a width of the X-rays is preferably sufficiently narrower than a width of the X-ray detection element 110. In this case, if there is no inflow or outflow of signals for the target element 11, it is considered that there are counts corresponding to $r_H(x)(P_H(x)+P_L(x))$ in the high energy range and $r_L(x)(P_H(x)+P_L(x))$ in the low energy range, and thus the proportions $\alpha_{H\_H}$, $\alpha_{H\_L}$, and $\alpha_{L\_L}$ may be expressed as in Equations (3-1) to (3-3).

$$\alpha_{H\_H} = \frac{P_H(m)}{r_H(x)(P_H(x) + P_L(x))} \quad (3\text{-}1)$$

$$\alpha_{H\_L} = \frac{P_L(m)}{r_H(x)(P_H(x) + P_L(x))} \quad (3\text{-}2)$$

$$\alpha_{L\_L} = \frac{P_L(m)}{r_L(x)(P_H(x) + P_L(x))} \quad (3\text{-}3)$$

Here, the parameters $\alpha_{H\_H}$, $\alpha_{H\_L}$, and $\alpha_{L\_L}$ for the target element 11 are calculated as being the same as parameters for the adjacent element 12. If the parameters are obtained in the above-described way, even in a case where a plurality of adjacent elements 12 are present around the target element 11, the parameters can be obtained at one time. On the other hand, needless to say, X-rays may be incident on the adjacent element 12 so that an outflow amount to the target element 11 is directly measured.

Figure 8:
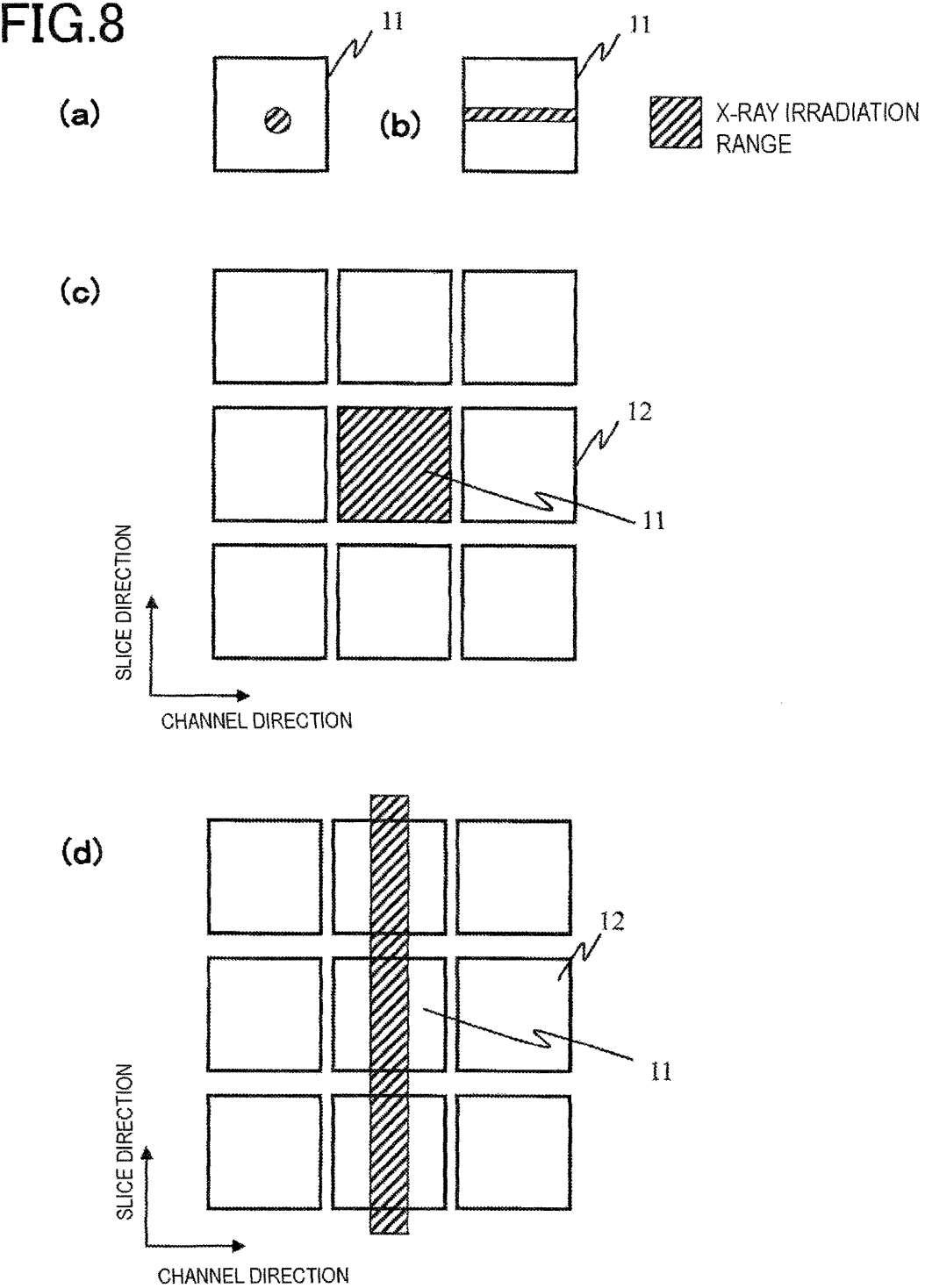
FIGS. 8(a) to 8(d) are diagrams illustrating details of a process S5011 in FIG. 7.

In FIG. 8, an adjacent element in one direction (for example, the channel direction) is assumed as the adjacent element 12, but, since an aspect ratio of detection elements or an element interval in the channel direction or the slice direction differs depending on a detector, the above-described actual measurement may be performed in both directions so that the respective parameters are obtained. Also in the actual measurement method, the proportions of counts in the high energy range and the low energy range $r_H(x)$ and $r_L(x)$ may be computed by obtaining a spectral distribution of X-rays through simulation.

The uncorrected digital output values $P_H(m)$ and $P_L(m)$ of the adjacent element 12 are used in Equations (3-1) and (3-3), but parameters can be determined with higher accuracy by taking into consideration energy shift in the adjacent element 12. In this case, in the adjacent element 12, digital output values $R_H(m)$ and $R_L(m)$ obtained by removing influence of energy shift may be calculated by using the previously measured proportions $\beta_{H\_L}(x)$ and $\gamma_{H\_L}(x)$ and Equations (4-1) and (4-2) which will be described later, and the parameters may be obtained according to Equations (3-1) to (3-3) by using the calculated digital output values instead of the digital output values $P_H(m)$ and $P_L(m)$.

The third method is a method for reducing a burden of performing actual measurement on all elements, and, for example, a small number of detection elements such as a detection element located at the center of the X-ray detector and a detection element located at an end thereof, parameters are determined according to the above-described actual measurement method, and, with respect to detection elements located therebetween, parameters are estimated through interpolation or simulation. Thus, it is possible to reduce a burden in the actual measurement method.

The parameters $\alpha_{H\_H}$, $\alpha_{H\_L}$, $\alpha_{L\_L}$, $\beta_{H\_L}(x)$, and $\gamma_{H\_L}(x)$ determined in the above-described manner are stored in the storage device 160, and are used for subsequent counting correction computation.

Figure 7:
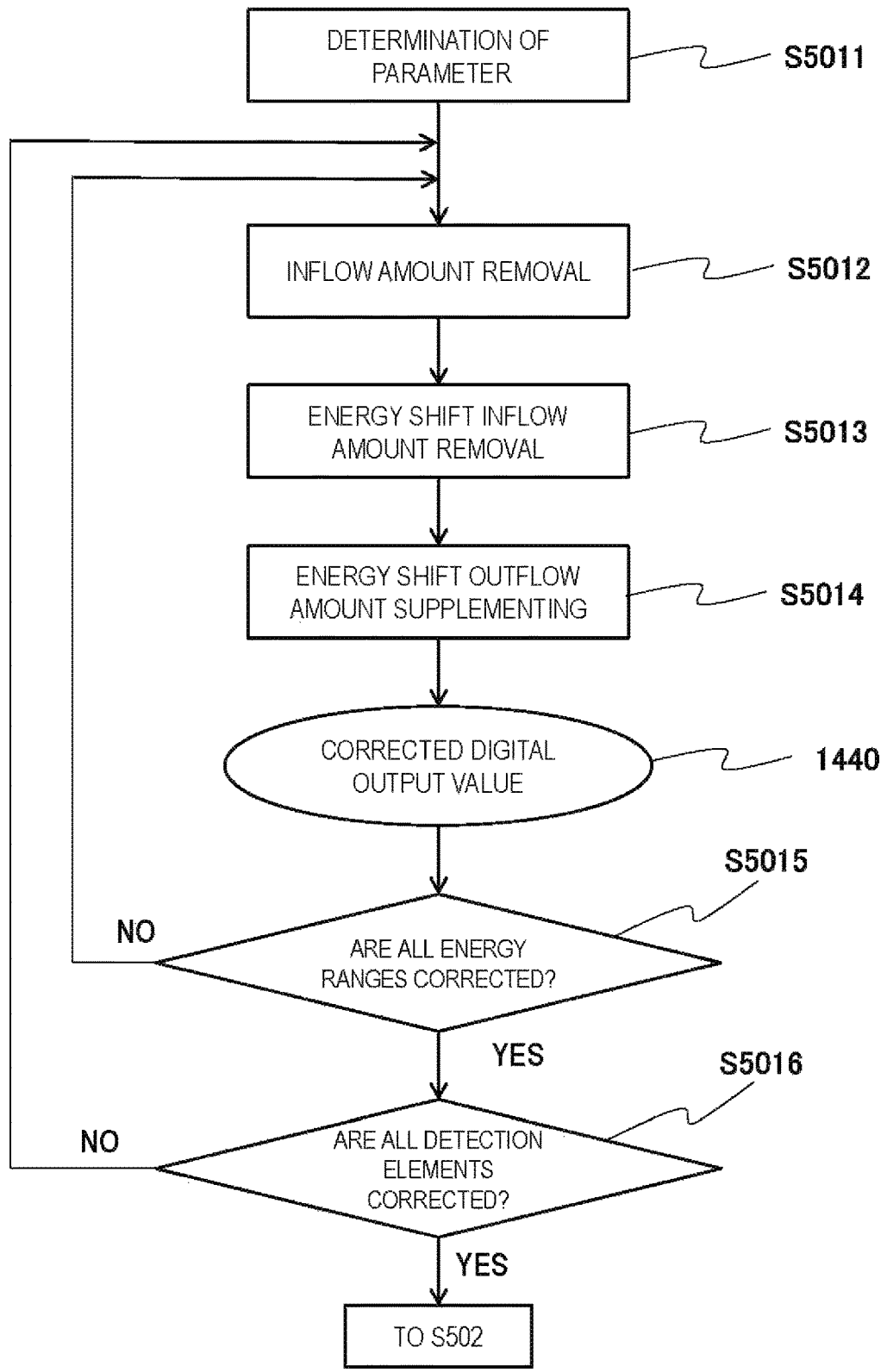
FIG. 7 is a diagram illustrating an example of a flow of correcting a counting in a first, embodiment.

<Inflow Amount Removal Process> (FIG. 7: S5012)

In the inflow amount removal process, in a case where a single X-ray photon is incident on the adjacent element 12 of the target element 11, and some signals generated at this time are detected in the target element 11, a wrongly counted number of the X-ray photon due to the signal which is incident from the adjacent element 12 is excluded from a counted number of X-ray photons in the target element 11 by also taking energy thereof into consideration.

Thus, the inflow amount calculation section 122 calculates a counted number measured in the target element 11 due to X-ray photons incident on the adjacent element 12, that is, a "photon inflow amount" in the above equations.

Here, digital output values in the high energy range and the low energy range before the inflow amount removal process is performed in the target element 11 are respectively indicated by $P_H(x)$ and $P_L(x)$, digital output values in the high energy range and the low energy range when energy of an incident X-ray photon is accurately measured are respectively indicated by $R_H(x)$ and $R_L(x)$, digital output values in the high energy range and the low energy range before the inflow amount removal process is performed in the adjacent element 12 are respectively indicated by $P_H(m)$ and $P_L(m)$, and digital output values in the high energy range and the low energy range when energy of an incident X-ray photon is accurately measured are respectively indicated by $R_H(m)$ and $R_L(m)$. In addition, x and m respectively indicate a position x of a correction target X-ray detection element and a position m of an adjacent element, and, needless to say, if a position of a target X-ray detection element is changed, the positions x and m are also changed.

In the high energy range of the target element 11, some of electric charge caused by photons incident on the high energy range of the adjacent element 12 outflows, and thus a counted number proportional to the number of photons is added thereto. This may be regarded as some of the signals 710 (proportion: $\alpha_{H\_H}$) in the high energy range of the adjacent element 12 flowing into the signals 610 in the high energy range of the target element 11 as illustrated in FIG. 6. Therefore, an inflow amount may be expressed by $\alpha_{H\_H}R_H(m)$. Similarly, in the low energy range of the target element 11, a counted number proportional to the number of photons incident on the high energy range of the adjacent element 12 and a counted number proportional to the number of photons incident on the low energy range of the adjacent element 12 are added thereto.

This may be regarded as some of the signals 710 (proportion: $\alpha_{H\_L}$) in the high energy range of the adjacent, element 12 flowing into the signals 620 in the low energy range of the target element 11 and some of the signals 720 (proportion: $\alpha_{L\_L}$) in the low energy range of the adjacent element 12 flowing thereinto, as illustrated in FIG. 6, and thus an inflow amount may be expressed by $\alpha_{H\_L}R_H(m)+\alpha_{L\_L}R_L(m)$. In this case, since there is no signal which is measured in the high energy range of the target element 11 among signals incident on the adjacent element 12 in the low energy range even if the whole energy of X-ray photons in the low energy range enters the target element 11, a proportion thereof is zero ($\alpha_{H\_L}=0$).

Therefore, an "inflow amount" as a digital amount to be corrected in the inflow amount removal process is $[R_H(m)\times\alpha_{H\_H}]$ for X-ray photons with the high energy, and is $[R_H(m)\times\alpha_{H\_L}+R_L(m)\times\alpha_{L\_L}]$ for X-ray photons with the low energy.

The counting correction portion 125 performs the inflow amount removal process according to the following Equations (4-1) and (4-2) by using the "amounts of inflow photons" calculated by the inflow amount calculation section 122

$$R_L(x)=P_L(x)-\alpha_{H\_L}R_H(m)-\alpha_{L\_L}R_L(m) \qquad (4\text{-}1)$$

$$R_H(x)=P_H(x)-\alpha_{H\_H}R_H(m) \qquad (4\text{-}2)$$

As mentioned above, a signal which flows into the target element 11 from the adjacent element 12 is subtracted from a signal value before the inflow amount removal process is performed, and thus a signal value when energy of incident X-ray photon is accurately measured can be measured.

<Energy Shift Inflow Amount Removal Process> (FIG. 7: S5013)

In an energy shift inflow amount removal process, when a single X-ray photon is incident on the target element 11, a counted number which is wrongly counted due to some of generated electric charge being detected by the target element 11 as an X-ray photon in an energy range lower than energy of the X-ray photon is corrected. This may occur in a case where detected some signals caused by X-ray photons are detected in the adjacent element 12, or energy of some X-ray photons is absorbed in the target element 11 but the photons are transmitted therethrough. This phenomenon may be regarded as some X-ray photons measured in the high energy range transitioning to the low energy range, and thus it may be regarded that a counted number flows into the low energy range from the high energy range as illustrated in FIG. 6.

In the energy shift inflow amount removal process, the energy shift inflow amount calculation section 123 calculates the number of X-ray photons flowing into the low energy range from the high energy range in order to exclude the number of X-ray photons flowing into the low energy range from the high energy range in counts in the low energy range. Here, as illustrated in FIG. 6, it may be regarded that some of the signals 610 in the high energy range flow into the signals 620 in the low energy range. Since a proportion thereof is $\gamma_{H\_L}(x)$, an inflow amount calculated by the energy shift inflow amount calculation section 123 is $\gamma_{H\_L}(x)R_H(x)$. This is subtracted from a signal value before the inflow amount removal process is performed according to Equation (5), and thus a signal value when energy of incident X-ray photon is accurately measured can be measured.

$$R_L(x)=P_L(x)-\gamma_{H\_L}(x)R_H(x) \qquad (5)$$

<Energy Shift Outflow Amount Supplementing Process> (S5014)

Next, in an energy shift outflow amount supplementing process, in contrary to the energy shift inflow amount removal process, a counted number in the high energy range is supplemented with a counted number measured in the low energy range. This amount (energy shift outflow amount) is $\beta_{H\_L}(x)R_H(x)$ similarly to the case of the energy shift inflow amount removal process. Therefore, the signal value before the inflow amount removal process is performed is supplemented with this value as in Equation (6), and thus a signal value when energy of incident X-ray photon is accurately measured can be measured.

$$R_H(x)=P_H(x)+\beta_{H\_L}(x)R_H(x) \qquad (6)$$

During the counting correction S501 in FIG. 5, the above-described inflow amount removal process S5012, energy shift inflow amount removal process S5013, and energy shift outflow amount supplementing process S5014 are all performed. In this case, the digital output values $R_H(x)$ and $R_L(x)$ in the high energy range and the low energy range when energy of an incident X-ray photon is accurately measured may be respectively expressed as in Equations (7-1) and (7-2).

$$R_L(x)=P_L(x)-\alpha_{H\_L}R_H(m)-\alpha_{L\_L}R_L(m)-\gamma_{H\_L}(x)R_H(x) \qquad (7\text{-}1)$$

$$R_H(x)=P_H(x)-\alpha_{H\_H}R_H(m)+\beta_{H\_L}(x)R_H(x) \qquad (7\text{-}2)$$

If L indicating the low energy range is set to 1, and H indicating the high energy range is set to 2, Equations (7-1) and (7-2) may be rewritten as in following equations.

If $n = 1$, $\qquad (8\text{-}1)$ $$P_n(x) = R_n(x) + \sum_{i=n}^{2} \alpha_{i\_n}R_i(m) + \sum_{i=n+1}^{2} \gamma_{i\_n}(x)R_i(x)$$

If $n = 2$, $\qquad (8\text{-}2)$ $$P_n(x) = R_n(x) + \sum_{i=n}^{2} \alpha_{i\_n}R_i(m) - \sum_{i=1}^{1} \beta_{n\_i}(x)R_n(x)$$

Equations (8-1) and (8-2) are equations corresponding to a case where the adjacent element 12 is treated as the target element 11, that is, since the two elements are handled, the equations are established in which the target element 11 and the adjacent element 12 are replaced with each other, and thus simultaneous equations of such a set of the equations are solved.

In this case, the equations are solved from a greater value of n (n=2), and thus the output values $R_H(x)$ and $R_L(x)$ can be calculated. In other words, if Equation (8-2) at n=2 is first solved, the third term $R_H(x)$ of the right side of Equation (8-1) is obtained and can thus be solved in the same manner as in Equation (8-2).

Figure 9:
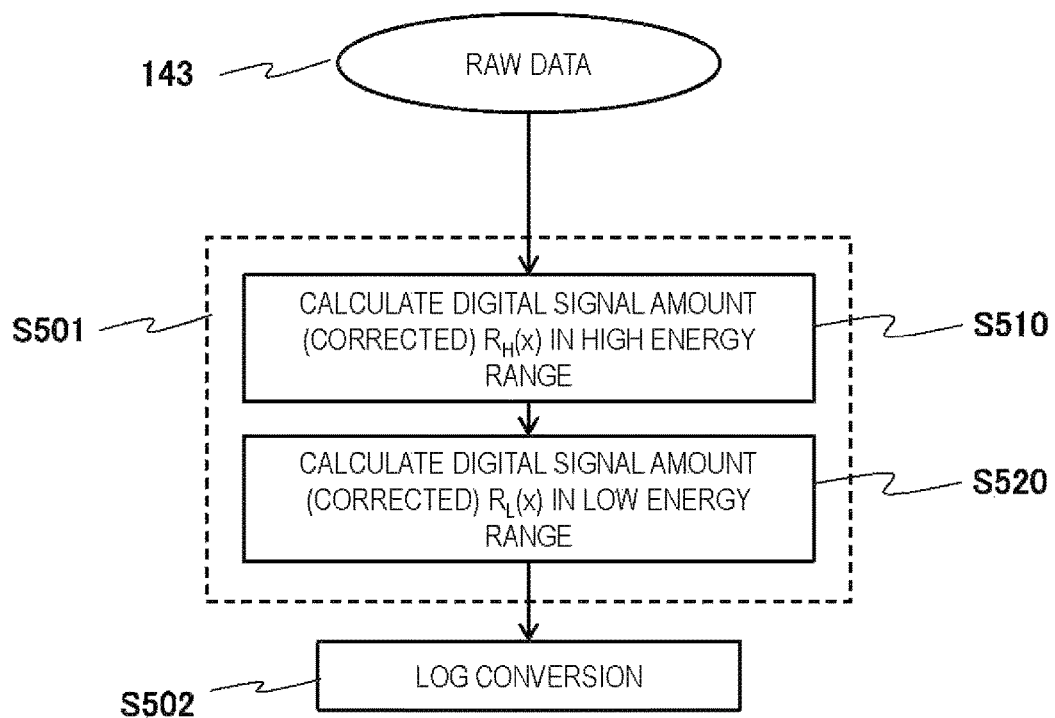
FIG. 9 is a diagram illustrating an internal computation order in processes S5012 and S5013 in FIG. 7.

FIG. 9 illustrates processes in the counting correction S501, in which such order of computation is taken into consideration. First, in a process S510, a corrected digital signal amount $R_2(x)$ (=$R_H(x)$) in the high energy range is calculated by using a digital signal amount $P_2(x)$ (=$P_H(x)$) in the high energy range in the raw data 143. In the process S510, computation is performed according to Equations (8-1) and (8-2) (at n=2) by using the parameters ($\alpha$, $\beta$, and $\gamma$) 141 stored in the storage device 160, and thus the inflow amount removal process and the energy shift outflow amount supplementing process are performed. Next, in the process S520, a corrected digital signal amount $R_1(x)$ ($R_L(x)$) in the low energy range is calculated by using the corrected digital signal amount $R_2(x)$ in the high energy range, previously obtained, and a digital signal amount $P_1(x)$(=$P_L(x)$) in the low energy range in the raw data 143. In the process S520, computation is performed according to Equations (8-1) and (8-2) (at n=1) by using the parameters ($\alpha$, $\beta$, and $\gamma$) 141 stored in the storage device 160, and thus the inflow amount removal process and the energy shift outflow amount supplementing process are performed so that corrected digital output values 1440 can be obtained with respect to the correction target element.

Through the counting correction S501 (S5012 to S5014), the digital signal amount $R_2(x)$ in the high energy range and the digital signal amount $R_1(x)$ in the low energy range can be obtained (S5015). These processes are performed on all elements forming the X-ray detector (S5016), and the flow proceeds to a process in LOG conversion S502. The subsequent processes are the same as described with reference to FIG. 5.

As described above, according to the present embodiment, the counting correction S501 is performed on a count difference caused by X-ray photons inflowing from the adjacent element 12 and a count difference caused by energy shift in the same element, and thus an accurate number of incident X-ray photons in each energy range can be obtained so that an accurate projection image can be obtained. An image can be prevented from being blurred due to inflow of a signal from the adjacent element, and thus it is possible to prevent a reduction in the resolution. It is possible to prevent a reduction in quantitativeness of a CT value or the occurrence of an artifact in a reconstructed image which is created on the basis of the projection image.

Modification Example 1 of First Embodiment

In the first embodiment, during the counting correction, three processes such as the inflow amount removal process, the energy shift inflow amount removal process, and the energy shift outflow amount supplementing process are all performed, but one or two processes may be omitted depending on characteristics or the like of a detector.

For example, in a case where crosstalk between elements is considerably slight and is thus within a negligible range, the inflow amount removal process (FIG. 7: S5012) may be omitted. In this case, the counting correction S501 is performed by using the above Equations (5) and (6), and the parameters $\beta_{H\_L}(x)$ and $\gamma_{H\_L}(x)$.

For example, in a case where energy shift in an element is within a negligible range, two processes such as the energy shift inflow amount removal process and the energy shift outflow amount supplementing process are omitted, and the counting correction S501 is performed by using the above Equations (4-1) and (4-2), and the parameter $\alpha$.

The invention also includes the counting correction S501 in which the inflow amount removal process and energy shift inflow amount removal process, the inflow amount removal process and the energy shift outflow amount supplementing process, only the energy shift inflow amount removal process, or only the energy shift outflow amount supplementing process is performed.

Even in a case where a single process is performed, the following effects can be achieved.

First, since the inflow amount removal process is performed, in a case where some signals generated due to incidence of X-ray photons to another X-ray detection element are detected in a certain X-ray detection element, the number of X-ray photons detected in other X-ray detection elements can be excluded through correction by taking energy of the X-rays into consideration, and thus accurate projection data can be obtained.

The energy shift inflow amount removal process is performed, and thus it is possible to calculate the number of X-ray photons measured in the low energy range due to the X-ray photons with higher energy being incident but only some energy being detected. Therefore, it is possible to exclude the number of X-ray photons in which X-ray photons in a higher energy range are wrongly detected in the low energy range from the number of X-ray photons measured in a certain energy range through correction, and thus accurate projection data can be obtained.

Since the energy shift outflow amount supplementing process is performed, the number of X-ray photons measured in a lower energy range due to only some energy being detected, can be calculated, and X-ray photons in a certain energy range can be supplemented with the calculated number of X-ray photons through correction, so that accurate projection data can be obtained.

In the first embodiment, as illustrated in the flow of FIG. 9, the corrected digital signal amount is calculated from the high energy range. This is because, as can be seen from Equation (7-1), the corrected high-energy digital signal amounts $R_H(x)$ and $R_H(m)$ are used to calculate the corrected low-energy digital signal amount $R_L(x)$. The second term and the fourth term of the right side of Equation (7-1) including $R_H(x)$ respectively indicate the inflow amount removal process and the energy shift inflow amount removal process. On the other hand, in the energy shift outflow amount supplementing process, the signal amount $R_H(x)$ is not required to obtain the signal amount $R_{LL}(x)$. Therefore, in a case where at least one of the inflow amount removal process and the energy shift inflow amount removal process is performed, the corrected digital signal amount is preferably obtained by using the digital signal amount $R_H(x)$ in the high energy range, and, in a case where only the energy shift outflow amount supplementing process is performed, the corrected digital signal amount may be obtained by using either of the digital signal amounts in the high energy range and the low energy range.

Modification Example 2 of First Embodiment

In the first embodiment, a description has been made of a case where parameters such as $\alpha_{H\_H}$, $\alpha_{H\_L}$, $\alpha_{L\_L}$, $\beta_{H\_H}(x)$, and $\gamma_{H\_L}(x)$ are obtained in advance, and are used as fixed values, but there may be a configuration in which the parameters are automatically or manually changed depending on scanning conditions or the like. The X-ray CT apparatus of the present embodiment is characterized in that a function of automatically or manually changing parameters is installed therein.

Figure 10:
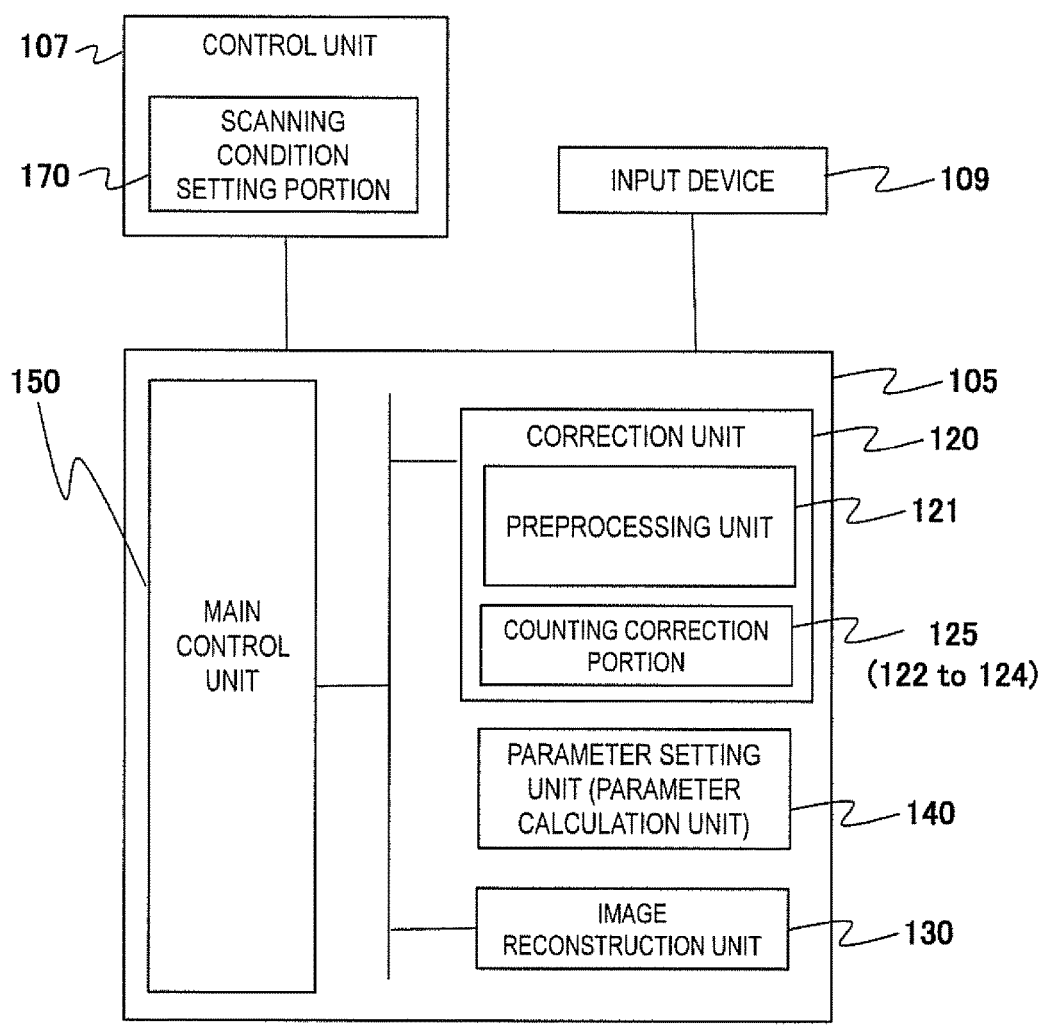
FIG. 10 is a functional block diagram according to a modification example of the first embodiment.

FIG. 10 illustrates examples of functional block diagrams of the control unit 107 and the central processing unit 105 of the present embodiment.

As illustrated, the control unit 107 includes a scanning condition setting portion 170. The parameter setting unit 140 of the central processing unit 105 functions as a parameter calculation unit in addition to the function illustrated in FIG. 4. In FIG. 10, the same elements as in FIG. 4 are given the same reference numerals, and description thereof will be omitted.

Although not illustrated in FIG. 10, the counting correction portion 125 is assumed to include at least one of the inflow amount calculation section 122, the energy shift inflow amount calculation section 123, and the energy shift outflow amount calculation section 124 illustrated in FIG. 4.

Scanning conditions such as the type of object, a tube voltage for irradiation, and the type of X-ray filter are set in the scanning condition setting portion 170 via the input device 109. The scanning condition setting portion 170 sends information regarding the set scanning conditions to the parameter setting unit 140 of the central processing unit 105. The parameter setting unit 140 determines the extent of hardness and softness of energy on the basis of the scanning conditions, and changes the parameters $\alpha_{H\_H}$, $\alpha_{H\_L}$, $\alpha_{L\_L}$, $\beta_{H\_H}(x)$, and $\gamma_{H\_L}(x)$.

Generally, energy changes (hardens or softens), for example, in a case where an energy distribution in a certain energy range changes due to transmission of X-rays through an object. Hardening or softening of the energy changes depending on the type of object, a tube voltage for irradiation, or the type of X-ray filter. The parameter setting unit 140 changes the parameters $\alpha_{H\_H}$, $\alpha_{H\_L}$, $\alpha_{L\_L}$, $\beta_{H\_L}(x)$, and $\gamma_{H\_L}(x)$ according to the change in energy, estimated on the basis of the scanning conditions. For example, in a case where energy in the high energy range is hardened, a braking distance till detection is lengthened, and thus $\alpha_{H\_H}$, $\alpha_{H\_L}$, $\beta_{H\_L}(x)$, and $\gamma_{H\_L}(x)$ may be increased. In a case where energy in the low energy range is hardened, a braking distance till detection is similarly lengthened, and thus $\alpha_{L\_L}$ may be increased. On the other hand, in a case where energy is softened due to an increase or the like in scattering rays, a braking distance is shortened, and thus the parameters may be reduced.

The parameter setting unit 140 may determine the extent of hardness or softness of energy on the basis of not only the information regarding the scanning conditions from the scanning condition setting portion 170 but also counted numbers in the high energy range and the low energy range, obtained from the signal collecting unit 108. Changing the parameters $\alpha_{H\_H}$, $\alpha_{H\_L}$, $\alpha_{L\_L}$, $\beta_{H\_L}(x)$, and $\gamma_{H\_L}(x)$ according thereto is the same as in the case of determination based on the scanning conditions.

FIG. 10 illustrates a case where the parameter setting unit 140 automatically changes the parameters by using the scanning conditions from the scanning condition setting portion 170, but there may be a configuration in which an operator directly inputs conditions for changing the parameters or energy dependence of the parameters via the input device 109. There may be a configuration in which the parameters $\alpha_{H\_H}$, $\alpha_{H\_L}$, $\alpha_{L\_L}$, $\beta_{H\_L}(x)$, and $\gamma_{H\_L}(x)$ are changed depending on factors other than hardness or softness of energy. For example, the parameters may be changed according to the visibility of an image.

Second Embodiment

A description has been made of a case where a signal inflows from only a single adjacent element 12 in the first embodiment, but the present embodiment is an embodiment in which inflow of signals from a plurality of adjacent elements 12 is taken into consideration.

Figure 11:
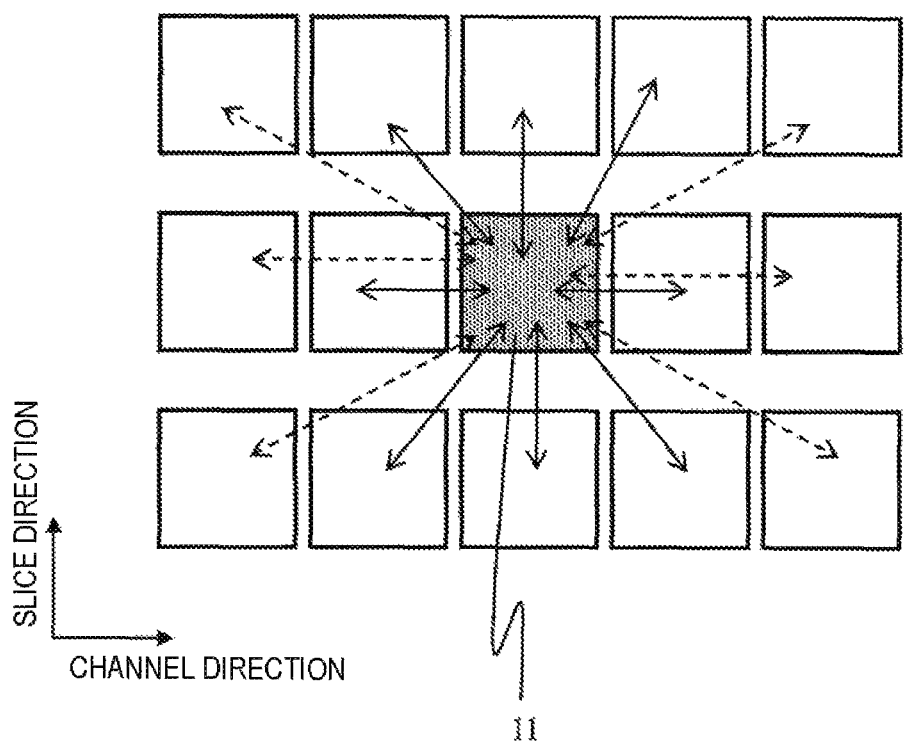
FIG. 11 is a diagram for explaining the concept of a second embodiment.

In the present embodiment, an adjacent element 12 may be adjacent to a target element 11, may not be directly adjacent thereto, and may be located at any position with respect to the target element 11. The adjacent element 12 may be all X-ray detection elements other than the target element 11 in the X-ray detector 104. FIG. 11 illustrates an example in which a range of the adjacent element 12 is widened. In FIG. 11, all elements connected via arrows are adjacent elements 12 of the target element 11.

In a case where all of a plurality of elements other than the target element 11 are adjacent elements 12, the influence of the plurality of adjacent elements 12 is a sum total of the influence of respective X-ray detection elements. Here, assuming that, among M X-ray detection elements from a first X-ray detection element to an M-th X-ray detection element, a single X-ray detection element, that is, an x-th X-ray detection element (where x is an integer of 1 or greater and M or smaller) is the target element 11, all X-ray detection elements other than the target element are the adjacent elements 12, and the above Equations (8-1) and (8-2) may be respectively rewritten as Equations (9-1) and (9-2).

If $n = 1$, (9-1)
$$P_n(x) = R_n(x) + \sum_{m=1, m \neq x}^{M} \sum_{i=n}^{2} \alpha_{i\_n}(m, x) R_i(m) + \sum_{i=n+1}^{2} \gamma_{i\_n}(x) R_i(x)$$

If $n = 2$, (9-2)
$$P_n(x) = R_n(x) + \sum_{m=1, m \neq x}^{M} \sum_{i=n}^{2} \alpha_{i\_n}(m, x) R_i(m) - \sum_{i=1}^{1} \beta_{n\_i}(x) R_n(x)$$

Here, in order to take into consideration a difference between proportions of inflow from the respective adjacent elements 12, a proportion in which a signal in the high energy range of an m-th adjacent element 12 (where m is an integer of 1 or greater and M or small other than x) flows into a signal in the high energy range of the target element 11 is indicated by $\alpha_{H\_H}(m,x)$. In other words, $\alpha_{H\_H}$ for a single adjacent element 12 is replaced with $\alpha_{H\_H}(m,x)$ in order to define a plurality of respective adjacent elements 12. Similarly, $\alpha_{H\_L}$ is replaced with $\alpha_{H\_L}(m,x)$, and $\alpha_{L\_L}$ is replaced with $\alpha_{L\_L}(m,x)$.

Such Equations (9-1) and (9-2) can be solved by using, for example, a matrix of M rows since there is a case where x is M from 1 to M. In this case, if the equations are solved from a greater value of n, Rn(x) (where n=1, ..., and N) of all n can be obtained in order.

The present embodiment is an embodiment in which a range of an adjacent element in the first embodiment is widened for generalization, and thus an accurate number of incident X-ray photons in each energy range can be obtained so that an accurate projection image can be obtained, in the same manner as in the first embodiment. Modification Examples 1 and 2 of the first embodiment are also applicable to the present embodiment.

Third Embodiment

The present embodiment is characterized in that an energy range is detected with respect to N (where N is an integer of 3 or greater) X-ray detector.

Figure 12:
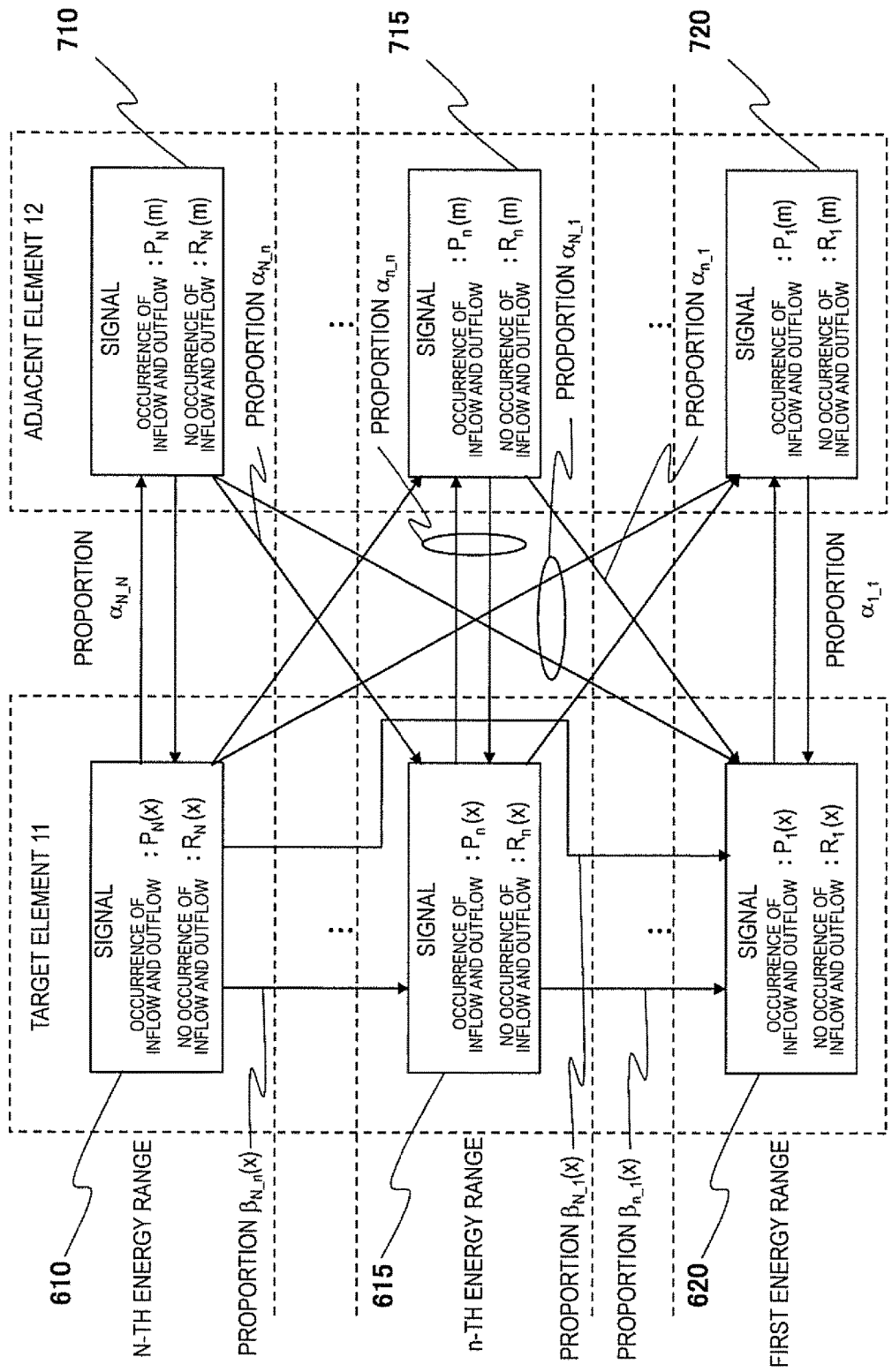
FIG. 12 is diagram illustrating Inflow and outflow of signals between elements and in the elements in a third embodiment.

A description will be made of exchange (inflow and outflow) of signals in the present embodiment with reference to FIG. 12. In FIG. 12, a signal in an N-th energy range of the target element 11 is indicated by a box 610, a signal in an n-th energy range is indicated by a box 615, and a signal in a first energy range is indicated by a box 620. Here, n is an integer of 2 to (N−1). Although not illustrated in FIG. 12, second to (N−1)-th energy ranges are present between the N and first energy ranges, and the n-th energy range is one thereof. The energy ranges indicate higher energy in order of the N-th, (N−1)-th, . . . , and first energy ranges.

Similarly, a signal in the N-th energy range of the adjacent element 12 is indicated by a box 710, a signal in the n-th energy range is indicated by a box 715, and a signal in the first energy range is indicated by a box 720. Here, in the same manner as in the target element 11, the second to (N−1)-th energy ranges are present between the N and first energy ranges, and the n-th energy range is one thereof.

In addition, in the same manner as in the first embodiment, a parameter $\alpha_{i\_j}$ (where i and j are integers of 1 to N satisfying i≥j) indicates a proportion in which a signal in an i-th energy range of the adjacent element 12 flows into a signal in a j-th energy range of the target element 11, a parameter $\beta_{i\_j}$ (where i and j are integers of 1 to N satisfying i≥j) indicates a proportion in which a signal flows out of the i-th energy range during inflow and outflow of signals between the i-th energy range of the target element 11 and the j-th energy range of the target element 11, and $\gamma_{i\_j}$ indicates a proportion in which a signal flows into the j-th energy range during the inflow and outflow of signals. The proportions also represent exchange among the N-th energy range, the n-th energy range, and the first energy range in FIG. 12, but, actually, there is the occurrence of inflow and outflow among all of the N-th, (N−1)-th, . . . , and first energy ranges.

With reference to FIG. 12, the signal 610 in the N-th energy range is focused. Only the signal 710 in the N-th energy range flows into the signal 610 in the highest energy range from the adjacent element 12. On the other hand, in the target element 11, there is no inflow from the other energy ranges, but there is outflow to the first to (N−1)-th energy ranges. Therefore, in the same manner as in the case of n=2 in the first embodiment, Pn(x) and Rn(x) in the signal 610 may be expressed as in Equation (10).

$$\text{If } n = N, \qquad (10)$$

$$P_n(x) = R_n(x) + \sum_{i=n}^{N} \alpha_{i\_n} R_i(m) - \sum_{j=1}^{N-1} \beta_{n\_i}(x) R_n(x)$$

Next, the signal 615 in the n-th energy range, (where n is an integer of 2 or greater and (N−1) or smaller) is focused. There is the occurrence of inflow from the n-th energy range (signal 715) to the N-th energy range (signal 710) from the adjacent element 12.

On the other hand, there is the occurrence of inflow from other energy ranges of the target element 11 such as the (n+1)-th energy range to the N-th energy range (signal 610), and there is the occurrence of outflow to each of the first energy range (signal 620) to the (n−1)-th energy range.

Therefore, Pn(x) and Rn(x) in the signal 615 in the n-th energy range may be expressed as in Equation (11).

$$\text{If } n = 2 \text{ to } (N-1), \qquad (11)$$

$$P_n(x) = R_n(x) + \sum_{i=n}^{N} \alpha_{i\_n} R_i(m) + \sum_{i=n+1}^{N} \gamma_{i\_n}(x) R_i(x) - \sum_{i=1}^{N-1} \beta_{n\_i}(x) R_n(x)$$

Next, the signal 620 in the first energy range which is the lowest energy range is focused. There is the occurrence of inflow from the first energy range (signal 720) to the N-th energy range (signal 710) from the adjacent element 12. On the other hand, there is the occurrence of inflow from other energy ranges of the target element 11 such as the second energy range to the N-th energy range, but there is no outflow to the other ranges. Therefore, Pn(x) and Rn(x) in the signal 620 may be expressed as in Equation (12).

$$\text{If } n = 1, \qquad (12)$$

$$P_n(x) = R_n(x) + \sum_{i=n}^{N} \alpha_{i\_n} R_i(m) + \sum_{i=n+1}^{N} \gamma_{i\_n}(x) R_i(x)$$

Figure 13:
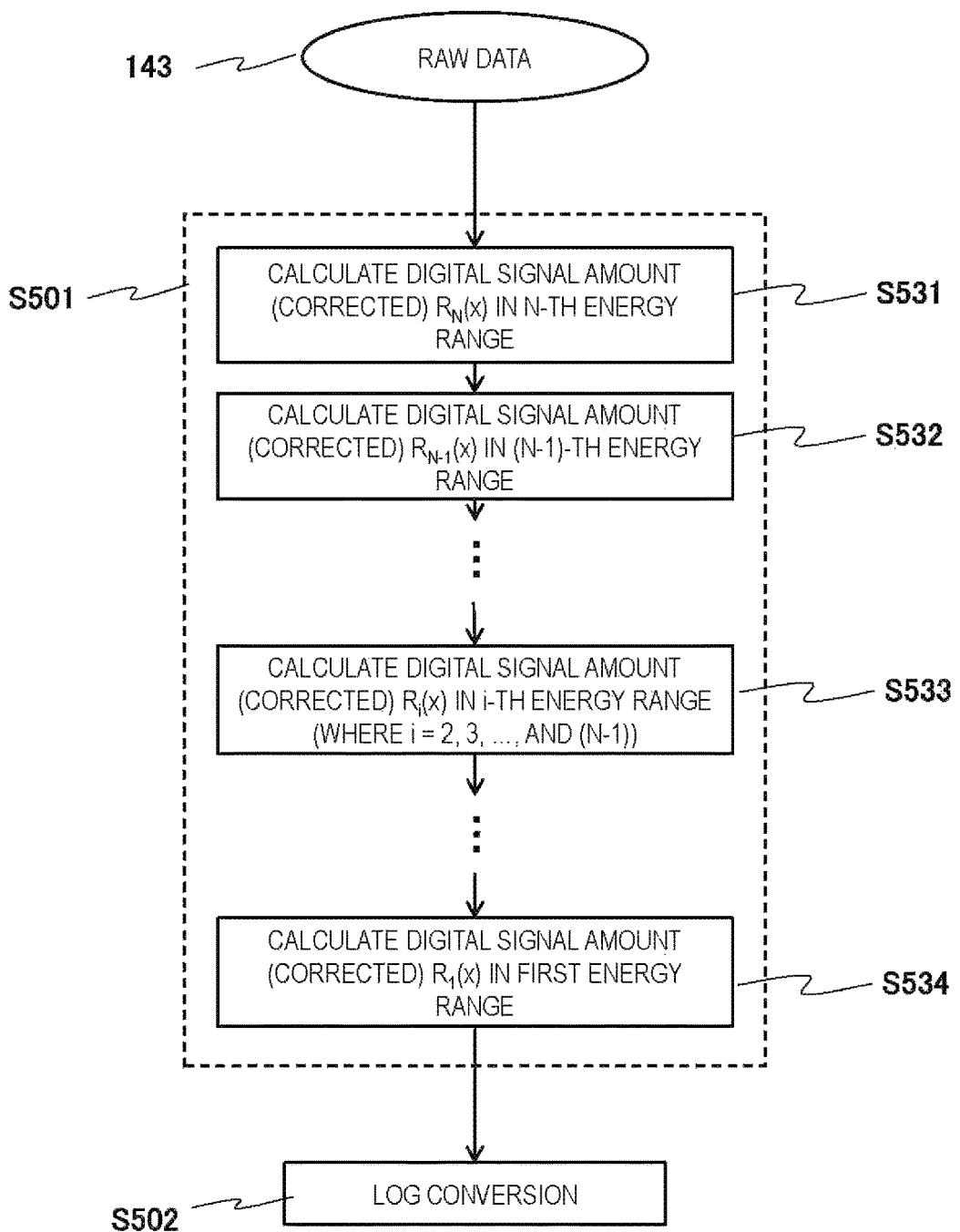
FIG. 13 is a diagram illustrating an example of a flow of counting correction in the third embodiment.

FIG. 13 illustrates processes in the counting correction portion 125, in which the above-described signal exchange is taken into consideration. First, in a process S531, a corrected digital signal amount Rn(x) in the N-th energy range is calculated by using a digital signal amount Pn(x) in the N-th energy range in the raw data 143. In the process S531, computation is performed according to Equation (10) by using the parameters ($\alpha$, $\beta$, and $\gamma$) 141 stored in the storage device 160, and thus the inflow amount removal process and the energy shift outflow amount supplementing process are performed. Here, Equation (10) relates to the target element 11, but is established for all of the other elements. If the X-ray detector 104 is formed of M X-ray detection elements 110, M equations are generated, and such simultaneous equations are solved so that a corrected digital signal amount Rn(x) (where x−1, . . . , and M) can be obtained. Here, needless to say, the adjacent element 12 is also included in the M X-ray detection elements 110.

Next, in a process S532, a corrected digital signal amount $R_{N-1}(x)$ in the (N−1)-th energy range is calculated by using the corrected digital signal amount $R_N(x)$ in the N-th energy range, previously obtained, and a digital signal amount $P_{N-1}(x)$ in the (N−1)-th energy range in the raw data 143. Also in the process S532, computation is performed according to Equation (11) by using the parameters ($\alpha$, $\beta$, and $\gamma$) 141 stored in the storage device 16C, and thus the inflow amount removal process, the energy shift inflow amount supplementing process, and the energy shift outflow amount supplementing process are performed.

In a process S533, the same process as in the process S532 is performed in order to calculate corrected digital signal amounts $R_i(x)$ (where i is an integer of 2 or greater and (N−2) or smaller) from the (N−1)-th energy range to the first energy range. In other words, in the process S533, computation is performed according to Equation (11) by using a digital signal amount $P_i(x)$ in the raw data 143, corrected $R_{i+1}(x)$, $R_{i+2}(x)$, . . . , and $R_N(x)$ in respective energy ranges from an (i+1)-th energy range to the N-th energy range, previously obtained, and the parameters ($\alpha$, $\beta$, and $\gamma$) 141 stored in the storage device 160, and thus the inflow amount removal process, the energy shift inflow amount supplementing process, and the energy shift outflow amount supplementing process are performed. Also in the processes S532 and S533, in the same manner as in the process S531, M simultaneous equations of Equation (11) are solved, and thus a corrected digital signal amount is obtained.

Finally, in a process S534, a corrected digital signal amount $R_1(x)(=R_L((x))$ in the first energy range is calculated. In the process S534, computation is performed according to Equation (12) by using corrected $R_2(x), R_3(x), \ldots,$ and $R_N(x)$ in respective energy ranges from the second energy range to the N-th energy range, previously obtained, and the parameters ($\alpha$, $\beta$, and $\gamma$) 141 stored in the storage device 160, and thus the inflow amount removal process and the energy shift inflow amount supplementing process are performed. Also in this process, M simultaneous equations obtained by applying Equation (12) to all the X-ray detection elements 110 are solved, and thus a corrected digital signal amount is obtained, As described above, the corrected digital signal amounts $R_1(x), R_3(x), \ldots,$ and $R_N(x)$ in respective energy ranges from the first energy range to the N-th energy range with respect to all of the correction target elements are obtained, and then the flow proceeds to a process in the LOG conversion S502. The subsequent processes are the same as described in the first embodiment (the flow illustrated in FIG. 5).

According to the present embodiment, in a case where there are a plurality of (two or more) energy ranges, the inflow amount removal process, the energy shift inflow amount removal process, and the energy sift outflow amount supplementing process can be performed, and thus an accurate number of incident X-ray photons in each energy range can be obtained. It is possible to prevent a counting error in the number of X-ray photons in the energy range as mentioned above, and thus an accurate projection image can be obtained. It is possible to prevent a reduction in quantitativeness of a CT value or the occurrence of an artifact in a reconstructed image which is created on the basis of the projection image.

Also in the present embodiment. Modification Examples 1 and 2 of the first embodiment are also applicable to the present embodiment. In other words, only one or two of the three processes included in the counting correction, that is, the inflow amount removal process, the energy shift inflow amount removal process, and the energy shift outflow amount supplementing process may be performed, and the parameters may be automatically or manually changed instead of fixed values.

Modification Example 1 of Third Embodiment

Also in the third embodiment, in the same manner as in the second embodiment, a range of adjacent elements 12 may be increased not only to an immediately adjacent element in the channel direction or the slice direction but also to a plurality of elements as illustrated in FIG. 11.

In other words, in the present embodiment, an adjacent element 12 may or may not be directly adjacent to a target element 11, and may be located at any position with respect to the target element 11. The adjacent element may be all X-ray detection elements other than the target element in the X-ray detector 104.

Assuming that, among M X-ray detection elements from a first X-ray detection element to an M-th X-ray detection element, a single X-ray detection element, that is, an x-th X-ray detection element (where x is an integer of 1 or greater and M or smaller) is a target element 11, the influence of a plurality of adjacent elements 12 is a sum total of respective X-ray detection elements if all X-ray detection elements other than the target element are adjacent elements 12, and thus the above Equations (10) to (12) may be respectively rewritten as Equations (1-1) to (1-3). In this case, an m-th (where m is an integer of 1 or greater and M or small other than x) parameter $a_{i\_j}$ (where i and j are integers satisfying $1 \leq i \leq j \leq N$) is indicated by $a_{i\_j}(m,x)$.

If $n = 2$ to $(N-1)$, (1-1)

$$P_n(x) = R_n(x) + \sum_{m=1, m \neq x}^{M} \sum_{i=n}^{N} \alpha_{i\_n}(m, x) R_i(m) + \sum_{i=n+1}^{N} \gamma_{i\_n}(x) R_i(x) - \sum_{i=1}^{N-1} \beta_{n\_i}(x) R_n(x)$$

If $n = N$, (1-2)

$$P_n(x) = R_n(x) + \sum_{m=1, m \neq x}^{M} \sum_{i=n}^{N} \alpha_{i\_n}(m, x) R_i(m) - \sum_{i=1}^{N-1} \beta_{n\_i}(x) R_n(x)$$

If $n = 1$, (1-3)

$$P_n(x) = R_n(x) + \sum_{m=1, m \neq x}^{M} \sum_{i=n}^{N} \alpha_{i\_n}(m, x) R_i(m) + \sum_{i=n+1}^{N} \gamma_{i\_n}(x) R_i(x)$$

These equations are obtained by expanding (generalizing) computation (Equations (7-1) and (7-21)) performed by the counting correction portion 125 in the first embodiment to a plurality of energy ranges and a plurality of adjacent elements.

Modification Example 2 of Third Embodiment

In the third embodiment, M-th order simultaneous equations such as Equations (10) to (12) are used to perform counting correction with respect to a plurality of energy ranges, but the correction may be performed through various approximations instead of using simultaneous equations.

As an example, approximate calculation may be performed on the basis of a detected digital output value $P_i(m)$ (where i=1, ..., and n) of the adjacent element 12. In this approximation (apxm), an inflow amount (Inflow am.) to the n-th energy range of the target element 11 is regarded as follows.

$$\text{Inflow am.} \sum_{i=n}^{N} \alpha_{i\_n} R_i(m) \rightarrow apxm \rightarrow \text{Inflow am.} \sum_{i=n}^{N} \alpha_{i\_n} P_i(m)$$

Consequently, Equations (10) to (12) may be respectively rewritten as the following Equations (13-1) to (13-3). In this case, the equations are solved from a larger value of n, and thus an inflow amount can be determined for each equation related to an energy range without simultaneous equations. This approximation is considerably useful when the number of energy ranges is larger or fast processing is desired to be performed.

If $n = N$, (13-1)

$$R_n(x) = \frac{P_n(x) - \sum_{i=n}^{N} \alpha_{i\_n} P_i(m)}{1 - \sum_{i=1}^{N-1} \beta_{n\_i}(x)}$$

If $n = 2$ to $(N - 1)$, (13-2)

$$R_n(x) = \frac{P_n(x) - \sum_{i=n}^{N} \alpha_{i\_n} P_i(m) - \sum_{i=n+1}^{N} \gamma_{i\_n}(x) R_i(x)}{1 - \sum_{i=1}^{N-1} \beta_{n\_i}(x)}$$

If $n = 1$, (13-3)

$$R_n(x) = P_n(x) - \sum_{i=n}^{N} \alpha_{i\_n} P_i(m) - \sum_{i=n+1}^{N} \gamma_{i\_n}(x) R_i(x)$$

When the corrected digital output value Rn(x) of a target element 11 is obtained, corrected digital output values of the other X-ray detection elements 110 are not used, and thus the digital output value is obtained without using simultaneous equations. However, in this case, $a_{i\_j}$ (where i and j are integers satisfying $1 \le i \le N$) is defined as a signal amount flowing into the target element 11 on the basis of a digital value $P_i(m)$ (where i=1, . . . , and n) of the adjacent element 12, and is required to be determined before actual measurement is performed.

As mentioned above, the embodiments of an X-ray scanning apparatus of the invention have been described by exemplifying the X-ray CT apparatus, but the invention is not limited thereto, and is applicable to all apparatuses mounted with a photon counting type radiation detector which classifies radiation incident on a detection element depending on energy and counts the number of photons. Examples of apparatuses to which the invention is applied may include an X-ray CT apparatus for non-destructive inspection, an X-ray cone-beam CT apparatus, a dual energy CT apparatus, an X-ray imaging diagnostic apparatus, an X-ray imaging apparatus, a fluoroscopic apparatus, a mammographic apparatus, a digital subtraction apparatus, a nuclear medicine examination apparatus, and a radiation therapy apparatus. The invention is not limited to an X-ray detector, and may also be applied to a photodetector which detects photons with various wavelengths. In this case, light may be visible light, infrared light, ultraviolet light, or gamma rays, and may have any wavelength.

The invention is not limited to the above-described embodiments, and may be variously modified and implemented in the implementation stage within the scope without departing the spirit thereof. The above-described embodiments include various steps, and thus various embodiments may occur through an appropriate combination of a plurality of disclosed constituent elements. For example, some constituent elements may be deleted from all the constituent elements described in the embodiments.

INDUSTRIAL APPLICABILITY

According to the invention, in an X-ray scanning apparatus mounted with a photon counting type radiation detector which classifies radiation incident on an X-ray detection element for each energy range, it is possible to correct a counting error of the number of X-ray photons in each energy range and thus to obtain an accurate projection image. In a CT apparatus mounted with the radiation detector, it is possible to prevent a reduction in quantitativeness of a CT value or the occurrence of an artifact.

REFERENCE SIGNS LIST

100 X-Ray Source, 101 Gantry Rotation Unit, 102 X-Ray Collimator, 103 Bed Top Plate, 104 X-Ray Detector, 105 Central Processing Unit, 106 Display Device, 107 Control Unit, 108 Signal Collecting Unit, 109 Input Device, 110 X-Ray Detection Element, 111 Detection Layer, 112 And 113 Electrode, 115 Reading Circuit, 120 Correction Unit, 121 Preprocessing Unit, 122 Inflow Amount Calculation Section, 123 Energy Shift Inflow Amount Calculation Section, 124 Energy Shift Outflow Amount Calculation Section, 125 Counting Correction Portion, 130 Image Reconstruction Unit, 140 Parameter Setting Unit, 160 Storage Device, 170 Scanning Condition Setting Portion

The invention claimed is:

1. An X-ray scanning apparatus comprising:
an X-ray detector that is formed of a plurality of photon counting type X-ray detection elements each of which detects an X-ray photon and classifies an energy level of the X-ray photon into a plurality of energy ranges to perform measurement;
a signal collecting unit that collects outputs from the X-ray detection elements so as to obtain digital output values; and
a data processing device that corrects the digital output values of the X-ray detection elements, and creates projection data by using the corrected digital output values, wherein the data processing device includes a correction unit that corrects a digital output value in each of the plurality of energy ranges with respect to each of the X-ray detection elements, and
wherein the correction unit includes an inflow amount calculation portion that calculates a digital amount corresponding to an amount of a signal which is caused by an X-ray photon incident on another X-ray detection element with energy equal to or higher than a detection target energy range of a single correction target X-ray detection element and which flows into the correction target X-ray detection element, and the correction unit removes the digital amount calculated by the inflow amount calculation portion from the digital output value.

2. The X-ray scanning apparatus according to claim 1,
wherein the inflow amount calculation portion calculates amounts of signals caused by X-ray photons in respective energy ranges from an n-th energy range to an N-th energy range, which are incident on an adjacent element which is adjacent to the correction target X-ray detection element, among digital signals measured in the n-th energy range (where n is an integer of 1 to N) of the correction target X-ray detection element.

3. The X-ray scanning apparatus according to claim 1,
wherein the correction unit corrects the digital output value in each of the plurality of energy ranges with respect to each of the X-ray detection elements in order from a higher energy range to a lower energy range.

4. An X-ray scanning apparatus comprising:
an X-ray detector that is formed of a plurality of photon counting type X-ray detection elements each of which detects an X-ray photon and classifies an energy level of the X-ray photon into a plurality of energy ranges to perform measurement;

a signal collecting unit that collects outputs from the X-ray detection elements so as to obtain digital output values; and a data processing device that corrects the digital output values of the X-ray detection elements, and creates projection data by using the corrected digital output values, wherein the data processing device includes a correction unit that corrects a digital output value in each of the plurality of energy ranges with respect to each of the X-ray detection elements, wherein the correction unit includes at least one of an energy shift inflow amount calculation portion that calculates a digital amount corresponding to an X-ray photon which energy-shifts from an energy range higher than a detection target energy range to the detection target energy range in a single X-ray detection element, and an energy shift outflow amount calculation portion that calculates a digital amount corresponding to an X-ray photon which is incident on a single X-ray detection element and energy-shifts to an energy range lower than the detection target energy range, and wherein the correction unit removes the digital amount calculated by the energy shift inflow amount calculation portion from the digital output value, or adds the digital amount calculated by the energy shift outflow amount calculation portion to the digital output value.

5. The X-ray scanning apparatus according to claim 4, wherein the energy shift inflow amount calculation portion calculates amounts of signals caused by X-ray photons in respective energy ranges from an (n+1)-th energy range to an N-th energy range, which are incident on a correction target X-ray detection element, among digital signals measured in the n-th energy range (where n is an integer of 1 to (N−1)) of the correction target X-ray detection element.

6. The X-ray scanning apparatus according to claim 4, wherein the correction unit further includes an inflow amount calculation portion that calculates a digital amount corresponding to an amount of a signal which is caused by an X-ray photon incident on another X-ray detection element with energy equal to or higher than a detection target energy range of a single correction target X-ray detection element and which flows into the correction target X-ray detection element, and the correction unit removes the digital amount calculated by the inflow amount calculation portion from the digital output value.

7. The X-ray scanning apparatus according to claim 4, wherein the energy shift outflow amount calculation portion calculates amounts of signals measured as signals in respective ranges from a first energy range to an (n−1)-th energy range of the correction target X-ray detection element among incident X-ray photons in an n-th energy range (where n is an integer of 2 to N) of the correction target X-ray detection element.

8. The X-ray scanning apparatus according to claim 4, wherein the correction unit corrects the digital output value in each of the plurality of energy ranges with respect to each of the X-ray detection elements in order from a higher energy range to a lower energy range.

9. An X-ray scanning apparatus comprising:
an X-ray detector that is formed of a plurality of photon counting type X-ray detection elements each of which detects an X-ray photon and classifies an energy level of the X-ray photon into a plurality of energy ranges to perform measurement;

a signal collecting unit that collects outputs from the X-ray detection elements so as to obtain digital output values; and a data processing device that corrects the digital output values of the X-ray detection elements, and creates projection data by using the corrected digital output values, wherein the data processing device includes a correction unit that corrects a digital output value in each of the plurality of energy ranges with respect to each of the X-ray detection elements, and wherein the correction unit includes a counting correction portion that corrects the digital output value by using a parameter indicating a movement proportion of X-ray photons, obtained in advance, between X-ray detection elements, and a parameter indicating an energy shift proportion in an X-ray detection element.

10. The X-ray scanning apparatus according to claim 9, wherein, when projection data in an n-th energy range (where n is an integer of 1 to N) of the X-ray detection elements is calculated, if the X-ray detection elements are set to M elements from first to M-th elements; an uncorrected digital output value of an x-th X-ray detection element (where x is an integer of 1 to M) is indicated by $P_n(x)$, an output value of the projection data is indicated by $R_n(x)$; a proportion of signals moving from an a-th X-ray detection element (where a is an integer of 1 to M) in an h-th energy range (where h is an integer of 1 to N) to a b-th X-ray detection element (where b is an integer of 1 to M) in an i-th energy range (where i is an integer of 1 to N) is indicated by $\alpha_{h\_i}(a,b)$; a proportion of outflow from a j-th energy range (where j is an integer of 1 to N) during inflow and outflow of signals between the j-th energy range and a k-th energy range (where k is an integer of 1 to N) in the X-ray detection elements is indicated by $\beta_{j\_k}(x)$; and a proportion of inflow to the k-th energy range is indicated by $\gamma_{j\_k}(x)$, the correction unit obtains the output value $R_n(x)$ of the projection data on the basis of the following Equations (1-1) to (1-3)

If $n = 2$ to $(N − 1)$, \hfill (1-1)

$$P_n(x) = R_n(x) + \sum_{m=1, m \neq x}^{M} \sum_{i=n}^{N} \alpha_{i\_n}(m, x) R_i(m) + \sum_{i=n+1}^{N} \gamma_{i\_n}(x) R_i(x) - \sum_{i=1}^{N-1} \beta_{n\_i}(x) R_n(x)$$

If $n = N$, \hfill (1-2)

$$P_n(x) = R_n(x) + \sum_{m=1, m \neq x}^{M} \sum_{i=n}^{N} \alpha_{i\_n}(m, x) R_i(m) - \sum_{i=1}^{N-1} \beta_{n\_i}(x) R_n(x)$$

If $n = 1$, \hfill (1-3)

$$P_n(x) = R_n(x) + \sum_{m=1, m \neq x}^{M} \sum_{i=n}^{N} \alpha_{i\_n}(m, x) R_i(m) + \sum_{i=n+1}^{N} \gamma_{i\_n}(x) R_i(x).$$

11. The X-ray scanning apparatus according to claim 9, further comprising:
a parameter changing unit that changes at least one of the parameters set for each of the energy ranges.

12. The X-ray scanning apparatus according to claim 11, further comprising:
an input device that receives an input operation performed by an operator,
wherein the parameter changing unit changes at least one of the parameters on the basis of an input operation on the input device.

13. The X-ray scanning apparatus according to claim 11, further comprising:
a scanning condition determination unit that determines at least one of the type of object, a tube voltage for irradiation, and the type of X-ray filter,
wherein the parameter changing unit changes at least one of the parameters on the basis of a result determined by the scanning condition determination unit.

14. The X-ray scanning apparatus according to claim 9, wherein the correction unit corrects a digital output value in each of the plurality of energy ranges with respect to each of the X-ray detection elements in order from a higher energy range to a lower energy range.

* * * * *